(12) United States Patent
Jang et al.

(10) Patent No.: US 11,530,422 B2
(45) Date of Patent: Dec. 20, 2022

(54) ONCOLYTIC VIRUS FOR TREATING BRAIN TUMORS USING RECOMBINANT NEWCASTLE DISEASE VIRUS INTO WHICH NEWCASTLE DISEASE VIRUS VECTOR-BASED PTEN GENE IS INSERTED AND COMPOSITION FOR TREATING BRAIN TUMORS USING SAME

(71) Applicant: LIBENTECH CO., LTD., Daejeon (KR)

(72) Inventors: Hyun Jang, Danwon-gu (KR); Bo Kyoung Jung, Busan (KR); Sung-Hoon Jang, Ansan-si (KR); Yong Hee An, Sejong (KR)

(73) Assignee: LIBENTECH CO., LTD., Daejeon (KR)

( * ) Notice: Subject to any disclaimer, the term of this patent is extended or adjusted under 35 U.S.C. 154(b) by 0 days.

(21) Appl. No.: 17/616,762

(22) PCT Filed: Jun. 3, 2021

(86) PCT No.: PCT/KR2021/006924
§ 371 (c)(1),
(2) Date: Dec. 6, 2021

(87) PCT Pub. No.: WO2022/203117
PCT Pub. Date: Sep. 29, 2022

(65) Prior Publication Data
US 2022/0364112 A1    Nov. 17, 2022

(30) Foreign Application Priority Data
Mar. 25, 2021   (KP) .................. 10-2021-0038880

(51) Int. Cl.
| | | |
|---|---|---|
| *C12N 15/86* | (2006.01) | |
| *A61P 35/00* | (2006.01) | |
| *C12N 9/16* | (2006.01) | |
| *C07K 14/005* | (2006.01) | |
| *A61K 38/00* | (2006.01) | |

(52) U.S. Cl.
CPC ............. *C12N 15/86* (2013.01); *A61P 35/00* (2018.01); *C07K 14/005* (2013.01); *C12N 9/16* (2013.01); *C12Y 301/03067* (2013.01); *A61K 38/00* (2013.01); *C07K 2319/00* (2013.01); *C12N 2760/18122* (2013.01); *C12N 2760/18133* (2013.01); *C12N 2760/18143* (2013.01); *C12N 2760/18171* (2013.01)

(58) Field of Classification Search
None
See application file for complete search history.

(56) References Cited

U.S. PATENT DOCUMENTS

2011/0052539 A1    3/2011   Stojdl et al.

FOREIGN PATENT DOCUMENTS

| JP | 2010-503660 A | 2/2010 |
| KR | 10-2020-0101065 A | 8/2020 |
| WO | 2005/051330 A2 | 6/2005 |
| WO | 2020/208609 A1 | 10/2020 |

OTHER PUBLICATIONS

Edris Shirvani et al., "Newcastle Disease Virus as a Vaccine Vector for SARS-CoV-2", Pathogens, Sep. 2020, 619, 8 pages.
Kaushik Benerjee et al., "Current Approaches for Glioma Gene Therapy and Virotherapy", Frontiers in Molecular Neuroscience, 2021, vol. 14, Article 621831, 30 pages.
Weina Sun et al., "Newcastle disease virus (NDV) expressing the spike protein of SARS-CoV-2 as a live virus vaccine candidate"; EBioMedicine 62 (2020); 103132 (9 pages).
Ziye Pan et al., "Identification of Optimal Insertion Site in Recombinant Newcastle Disease Virus (rNDV) Vector Expressing Foreign Gene to Enhance Its Anti-Tumor Effect"; PLOS One; vol. 11(10) E0164723; Oct. 13, 2016 (14 pages).
Shobana Raghunath; "Targeted Oncolytic Virotherapy Using Newcastle Disease Virus Against Prostate Cancer"; Dissertation submitted to the faculty of the Virginia Polytechnic Institute and State University; Sep. 24, 2012; (192 pages).
Notification of Reason for Refusal dated Jun. 29, 2021 for related Korean Patent Application No. 10-2021-0038880.
Decision to Grant a Patent dated Nov. 29, 2021 for related Korean Patent Application No. 10-2021-0038880.

*Primary Examiner* — James D Schultz
*Assistant Examiner* — Kimberly A Aron
(74) *Attorney, Agent, or Firm* — Sughrue Mion, PLLC

(57) ABSTRACT

Provided are an oncolytic virus for treating brain tumors using a recombinant Newcastle disease virus into which a Newcastle disease virus (NDV) vector-based PTEN (phosphatase and tensin homolog) gene is inserted and a composition for treating brain tumors using the same which can be used for a therapeutic viral agent that can induce reduction of clinical symptoms or partial or complete remission through brain tumor cell death or brain tumor tissue reduction by expressing normal PTEN protein after being infected with brain tumor cells, as a recombinant Newcastle disease virus containing a human PTEN protein gene.

7 Claims, 6 Drawing Sheets

Specification includes a Sequence Listing.

FIG. 1A

NDV VG/GA-strain

```
Pmel    SacII   (4925)      SpeI              MluI        PacI
        (2358)  KasI        (8095)            (13043)
                                                            15,186
   F5      F4
                   F3            F2                  F1
```

F1-F2-F3-F4-F5
-pBR322

SEQUENCE LISTING

```
<160> NUMBER OF SEQ ID NOS: 53

<210> SEQ ID NO 1
<211> LENGTH: 19091
<212> TYPE: DNA
<213> ORGANISM: Artificial Sequence
<220> FEATURE:
<223> OTHER INFORMATION: LVP-K1

<400> SEQUENCE: 1
accaaacaga gaatccgtaa ggtacgatag aaggcgaagg agcaatcgaa gtcgtacggg      60
tagaaggtgt gaatctcgag tgcgagcccg aagctcaaac tcgagagagc cttctgccaa     120
aatgtcttct gtattcgatg agtacgagca gctcctcgcg gctcagactc gccccaatgg     180
agctcatggc ggaggagaga aggggagcac cttaaaggta gaagtcccgg tattcactct     240
caacagtgat gacccagaag atagatggaa cttcgcagtg ttttgtcttc ggattgctgt     300
tagcgaggat gccaacaaac cacttaggca aggtgctctc atatctctct tatgttccca     360
ctctcaagtg atgaggaacc atgttgccct tgcgggaaa cagaatgagg ccacactggc      420
tgttcttgag atcgatggtt ttaccaacgg cgtgcccag ttcaacaaca ggagtggagt      480
gtctgaagag agagcacaga gatttatgat gatagcaggg tctctcccctc gggcatgcag     540 caacggtacc ccgttcgtca cagctggggt tgaagatgat gcaccagaag acattactga     600
```

```
taccctggag aggatcctct ctatccaggc tcaagtatgg gtcacggtgg caaaggccat      660
gactgcatat gagacagcag atgagtcaga aacaagaaga atcaataagt acatgcagca      720
aggcagggtc cagaagaagt acatcctcca ccccgtatgc aggagcgcaa tccaactcac      780
aatcagacag tctctggcgg tccgcatctt tttggttagc gagcttaaga gaggccgcaa      840
cacggcaggt gggacctcca cctattacaa cttggtgggg gatgtagact catacatcag      900
gaacactggg ctaactgcat tcttcctgac acttaaatat ggaattaaca ccaagacatc      960
agcccttgca cttagcagcc tctcaggcga tatccagaaa atgaagcagc tcatgcgctt     1020
gtatcggatg aaaggagata atgcgccgta catgacattg ctcggtgaca gtgaccagat     1080
gagctttgca cctgccgagt atgcacaact ttactccttt gccatgggta tggcatcagt     1140
cctagataaa ggaactagca aataccaatt tgccagggac tttatgagca catcattctg     1200
gagacttgga gtagagtacg ctcaggctca aggaagtagc atcaatgagg atatggccgc     1260
cgagctaaag ctaaccccag cagcaaggag aggcctggca gctgctgccc aaagagtgtc     1320
tgaggagacc agcagcatgg acatgcccac ccaacaagcc ggggtcctca ctggactcag     1380
cgacggaggc tcccaagccc ccaggtgc actgaacaga tcacaaggc aaccggacac       1440 cggggatggg gagacccaat ttctggatct gatgagagcg gtggcaaata gcatgagaga     1500
agcgccaaac tctgcgcagg gcaccctca accgggcct cccccaaccc ctgggcctc       1560 tcaagacaat gacaccgact gggggtactg accgacagca cccagtttgc ttctatgagg     1620
tcatcccaat tcctctgctt agaaaaaata cgggtagaag cggccgcggc cggcccaca     1680 ccccaccct caatccgcaa tcccgcatgg ccaaacccac aaacgaaccc cctgtctcc      1740 ctcctctccc ccagcccac aaccccacct gcccagggca acataggtac aatgcgaccc     1800
actaataatc aatacagggc caaagaaatt agaaaaaagt acgggtagaa gggagacatt     1860
cagagatcag ggcgagtcac ccgggtctct gctctccctt ctaccagtg gattaggatg     1920 gagatggcca cctttacaga tgcggagatc gacgagctat ttgagaccag tggaactgtc     1980
attgacagca taattacggc ccagggaaaa ccagtagaga ctgttggaag gagtgcaatc     2040
ccacaaggca aaactaaggc tttgagcgca gcatgggaga agcatgggag catccagtca     2100
ccagccagcc aagacacccc tgatcgacag gacagatcag ataaacaact gtccacaccc     2160
gagcaagcga gtccaaacga cagcccccca gccacatcca ctgaccagcc tcccactcag     2220
gctgcagatg aggccggcga tacacagctc aagaccggag caagcaactc tctgctgtcg     2280
atgcttgata aactcagcaa taagtcatct aatgctaaaa agggcccagg gtcgagccct     2340
caagaaaggc atcatcaacg tctgactcaa caacagggga gtcaacaaag ccgcggaaac     2400
agccaagaga gaccgcagaa ccaggccaag gccatccctg gaaaccaggt cacagacgcg     2460
aacacagcat atcatggaca atgggaggag tcacaactat cagctggtgc aacccatcat     2520
gctctccgat cagagcagag ccaagacaat actcctgcac ctgtggatca tgtccagcta     2580
cctgtcgact ttgtgcaggc gatgatgtct atgatggagg cgatatcaca gagggtaagt     2640
aaagttgact atcagctgga ccttgtcttg aaacagacat cttctatccc catgatgcgg     2700
tctgaaatcc agcagctgaa aacgtctgtt gcggtcatga agccaatttt ggcatgatg      2760 aagatcctgg accctggttg tgccaacgtt tcatctctaa gtgatctacg ggcagttgcc     2820
cgatcccacc cggttttaat ttctggcccc ggagacccat ctcctatgt gacccaaggg     2880 ggcgaaatgg cactcaataa actttcgcaa ccggtgcaac accctctga attgattaaa      2940
```

```
cccgccacgg caagcgggcc tgatatagga gtggagaaag acactgtccg tgcattgatc    3000
atgtcacgcc ctatgcatcc gagctcttca gctaggctct tgagcaaact ggacgcagcc    3060
ggatcgattg aggaaatcag aaaaatcaag cgccttgcac tgaatggcta atcaccaccg    3120
caacccgcag cagatccctg tccacccagc accacgggt atctgcacca agctcctctc    3180
tgcaaaccca aggtccaaca ccccgagcga caaccctgtc ctgcttcctc tgccccacta    3240
aatgatcgcg cagctgcaat caattcagct atattaagga ttaagaaaaa atacgggtag    3300
aatcggagtg ccccgattgt gccaagatgg actcatctag gacaatcggg ctgtactttg    3360
attctaccct tccttctagc aacctgctag cattcccgat agtcctacaa gacacagggg    3420
acgggaagaa gcaaatcgcc ccgcaataca ggatccagcg tcttgactcg tggacagaca    3480
gcaaagaaga ctcggtattc atcaccacct atggattcat ctttcaggtt gggaatgaag    3540
aagccactgt cggcatgatc aatgataatc ccaagcgcga gttactttcc actgccatgc    3600
tatgcctagg gagtgtacca aatgtcggag atcttgttga gctggcaagg gcctgcctca    3660
ctatggtggt aacatgcaag aagagtgcaa ctaacaccga gagaatggtc ttctcagtag    3720
tgcaggcacc ccaggtgctg caaagctgta gggttgtggc aaacaaatac tcgtcggtga    3780
atgcagtcaa gcacgtgaaa gcaccagaga agattcctgg gagcggaacc ctagagtaca    3840
aagtgaactt tgtctctctg accgtggtgc caagaaagga cgtctacaag ataccaactg    3900
cagcacttaa ggtctctggc tcaagtctgt acaatcttgc gctcaatgtc actattgatg    3960
tggaggtaga cccgaagagc ccgttggtca atccctttc caagtccgac agtgggtact    4020
atgctaatct cttcttacat attgggctta tgtccactgt agataagaag gggaagaaag    4080
tgacatttga caagctggaa aggaagataa ggagacttga tctatctgta gggcttagtg    4140
acgtgctcgg accttccgtg cttgtaaagg cgagaggtgc acggactaag ctgctggcac    4200 cttttcttctc tagcagtggg acagcctgct atcccatagc aaatgcctct cctcaggtgg    4260
ccaagatact ctggagccaa accgcgtacc tgcggagtgt aaaagtcatt atccaagcgg    4320
gcacccagcg tgctgtcgca gtgaccgccg accacgaggt tacctctact aagctggaga    4380 agggcatac cattgccaaa tacaatccct tcaagaaata ggctgcatct ctgagattgc    4440
actccgccca tcttcccgga tcaccatgac actaaataat gatctgtctt gattacttat    4500
agttagttcg cctgtctatc aaattagaaa aaacacgggt agaagattct ggatcccggt    4560
tggcgccttc aaggtgcaag atgggctcca gatcttctac caggatccca gtacctctta    4620
tgctgaccgt ccgagtcatg ttggcactga gttgcgtctg tccgaccagc gcccttgatg    4680
gcaggcctct tgcagctgca gggattgtgg taacaggaga caaagcagtc aacatataca    4740
cctcatctca gacagggtca atcataatca agttactccc aaatatgccc aaggataaag    4800
aggcgtgtgc aaaagccccg ttggaggcat acaacaggac attgactact tgctcaccc    4860 cccttggtga ttctatccgt aggatacaag agtctgtgac cacgtccgga ggagggaaac    4920
agggacgtct tataggcgcc attatcggtg gtgtagctct cggggttgca accgctgcac    4980
agataacagc agcctcggct ctgatacaag ccaatcaaaa tgctgccaac atactccggc    5040
taaaagagag cattgctgca accaatgagg ctgtgcacga ggtcactaat ggattatcac    5100
aactagcagt ggcagttggg aagatgcagc aatttgttaa tgaccagttt aataaaacag    5160
ctcaggaatt ggactgtata aaattacac agcaggttgg tgtagaactc aacctgtacc    5220
taactgaatt gactacagta ttcgggccac aaatcacttc ccctgcctta actcagctga    5280
ctatccaggc gctttacaat ctagctggtg ggaatatgga ttacttgttg actaagttag    5340
```

```
gtgtggggaa caaccaactc agctcattaa ttagtagtgg cctgatcacc ggcaacccta    5400
ttctgtacga ctcacagact caactcttgg gtatacaggt aaccctaccc tcagtcggga    5460
acctaaataa tatgcgtgcc acctacctgg aaaccttgtc tgtaagtaca accaaaggat    5520
ttgcctcagc acttgtccca aaagtagtga cacaggtcgg ttccgtgata gaagagcttg    5580
acacctcgta ctgtatagag accgatttgg atctatattg tacaagaata gtgacattcc    5640
ctatgtctcc tggtatttat tcctgtttga gtggcaatac atctgcttgc atgtactcaa    5700
agactgaagg cgcactcact acgccgtata tgaccctcaa aggctcagtt attgctaact    5760
gtaagatgac aacatgtaga tgtgcagacc ccccgggtat catatcgcaa aattatggag    5820
aagctgtgtc tctaatagat aggcaatcat gcaatatctt atccttagac gggataactt    5880
tgaggctcag tggggaattt gatgcaactt atcaaaagaa tatctcaata caagattctc    5940
aagtaatagt gacaggcaat cttgatatct cgactgagct tgggaatgtc aacaactcga    6000
taagtaatgc tttggataag ttagaggaaa gcaacagcaa actagataag gtcaatgtca    6060
aactgaccag cacatccgct cttattacct atatcgtttt aactgtcata tctcttgtat    6120
gtggtatact tagcctggtt ctagcatgct acctgatgta caagcaaaag gcgcaacaga    6180
agaccttgtt gtggcttggg aataataccc tagaccagat gagggccact acaaaaatgt    6240
gaatgcggat gagaggcaga acatcccca atagcagttt gtgtgtaaag tctgacagcc    6300
tgttaattag aagaattaag aaaaaactac cggatgtaga tgaccaaagg gcgatatacg    6360
ggtagaacgg tcggggaggc cgtccctcaa tcgggagccg ggcctcacaa catccgttct    6420
accgcatcac caatagcagt tttcagtcat ggaccgcgca gttagccaag ttgcgctaga    6480
gaatgatgaa agagaggcaa agaatacatg gcgcttggta ttccggatcg caatcctact    6540
ctcaacggtg gtgaccttag ccatctctgc agccgccctt gcatatagca tggaggccag    6600
cacacctagc gatcttgtag gcataccgac tgcgatctct agagcagagg aaaagattac    6660
atctgcactc ggttccaatc aagatgtagt agataggata tataagcagg tggccctcga    6720
atctccactg gcattgctaa acaccgaatc tacaattatg aacgcaataa cgtctctctc    6780
ttatcgaatc aatggggccg caaatagcag cggatgtgga gcacccattc atgatccaga    6840
ttatattgga ggaataggta aagaacttat tgtagatgat gctagcgacg tcacatcata    6900
ctatccctct gcgttccaag aacacctgaa ctttatcccg gcgcctacta caggatcagg    6960
ttgcactcgg ataccctcat ttgacatgag cgctacccac tactgttata ctcacaatgt    7020
gatattatct ggctgcagag atcactcgca ctcacatcaa tatttagcac ttggtgtgct    7080
tcggacatct gcaacaggga gggtattctt ttccactctg cgttccatca atctggatga    7140
cacccaaaat cggaagtctt gcagtgtgag tgcaaccccc ttgggttgtg atatgctgtg    7200
ctctaaagtc acagagactg aagaagagga ttataactca gctatcccca cgtcgatggt    7260
acatggaagg ttagggttcg acggccaata ccacgagaag gacctagatg tcacaacact    7320
attcgaggac tgggtggcaa actacccagg agtaggggc gggtctttta ttgacaaccg    7380
cgtatggttc ccagtttacg gagggctaaa acccaattcg cccagtgaca ccgcacaaga    7440
agggaaatat gtaatataca agcgatacaa tgacacatgt ccagatgagc aagattatca    7500
gattcaaatg gctaagtctt catataagcc tgggcggttt ggagggaaac gcgtacagca    7560
ggccatctta tctatcaaag tgtcaacatc cttgggcgag gacccggtac tgactgtacc    7620
gcccaacaca gtaacactca tggggccgaa aggcagagtt ctcacagtag ggacatctca    7680
```

-continued

```
tttcctttat cagcgagggt catcatactt ctcccctgcc ctactatatc ctatgatagt    7740
cagcaacaaa acagccactc ttcatagtcc ttatacattc aatgccttca ctcgaccagg    7800
tagtgtccct tgccaggctt cagcaagatg ccctaactca tgtgttaccg gagtctatac    7860
tgatccatat cccttggtct tctataggaa ccacaccttg cgaggggtat tcgggacgat    7920
gcttgatgat aaacaagcaa gactcaaccc tgtatctgca gtatttgaca gcatatcccg    7980
cagtcgcata acccgggtga gttcaagcag caccaaggca gcatacacaa catcaacatg    8040
ttttaaagtt gtaaagacca ataaaaccta ttgtctcagc attgccgaaa tatccaatac    8100
cctcttcggg gaattcagaa tcgtcccttt actagttgag attctcaagg atgatggggt    8160
tagagaagcc aggtctagcc ggttgagtca actgcgagag ggttggaaag atgacattgt    8220
atcacctatc ttttgcgacg ccaagaatca aactgaatac cggcgcgagc tcgagtccta    8280
cgctgccagt tggccataat cagctagtgc taatgtgatt agattaagtc ttgtcggtag    8340
tcacttgatt aagaaaaaat gtgggtggta gcgggatata aggcaaaaca actcaaggag    8400
gatagcacgg gtaggacatg gcgagctccg gtcccgagag ggcggagcat cagattatcc    8460
taccagagtc acacctgtct tcaccattag tcaagcacaa actactctat tactggaaat    8520
taactgggct accactccct gacgagtgtg acttcgacca cctcattctc agccacaat    8580
ggaagaaaat acttgaatcg gcctcccctg acactgagag aatgataaaa cttggaaggg    8640
cagtgcacca gactctcaac cacaattcca agataaccgg agtactccat cccaggtgtt    8700
tagaagaatt ggctagtatt gaggttcctg actcaaccaa caagtttcgg aagatcgaga    8760
agaaaatcca aattcacaac acaaggtatg gagaactgtt cacaagactg tgcacgcatg    8820
tagagaagaa attgttggga tcatcttggt ctaataatgt cccccggtca gaagagttca    8880
acagcatccg tacagatccg gcattctggt ttcactcaaa atggtccaca actaagtttg    8940
catggctcca tataaaacag attcaaaggc atctgattgt ggcagcaaga acaaggtccg    9000
cagccaacaa attggtgacg ctgacccata aggtaggcca agtctttgtt actcctgagc    9060
ttgtcattgt gacacataca gatgagaaca agttcacgtg tcttacccag gaacttgtgt    9120
tgatgtatgc agatatgatg gagggcagag atatggtcaa cataatatca tccacggcgg    9180
cacatctcag gagcctatca gagaaaattg atgacattct gcggttagta gatgccctgg    9240
caaaagatct gggtaatcaa gtctacgatg ttgtagcact catggaggga tttgcatacg    9300
gcgccgtcca gctgcttgag ccgtcaggta cattcgcagg ggatttcttc gcattcaacc    9360
tgcaggagct caaagacact ttgatcggcc tccttcctaa ggatatagca gaatctgtga    9420
ctcacgcaat agccactgta ttctctggct tagaacaaaa tcaagcggct gagatgctgt    9480
gcctgttgcg tctatggggc cacccattac ttgagtcccg tattgcggca aaagcagtaa    9540
ggagccaaat gtgcgcacca aaaatggtag actttgatat gatcctccag gtattgtctt    9600
tctttaaagg aacaatcatc aacggataca gaaagaagaa tgcaggtgtt tggccacgtg    9660
tcaaagtaga tacgatatac gggaaggtca ttgggcagct acacgctgat tcagcggaga    9720
tttcacacga tatcatgttg agagagtaca agagtttatc tgcgcttgaa ttcgagccat    9780
gtatagaata cgaccctatc accaatctga gcatgtttct aaaagacaag gcgatcgcac    9840
acccgaaaga caactggctc gccgcgttta ggcgaaacct tctctctgag gaccagaaga    9900
aacatgtaaa ggaggcaacc tctactaacc gtctcttgat agagttctta gagtcaaatg    9960
attttgatcc atataaggag atggaatatc tgacgaccct tgagtaccta agagatgaca   10020
atgtggcagt atcatactcg ctcaaggaga aggaagtgaa ggttaatggg cggattttg   10080
```

```
ctaagctaac aaagaaatta aggaactgtc aagtgatggc ggaagggatc ttagctgacc    10140
agattgcacc tttctttcaa gggaatgggg tcattcagga tagcatatct ttaaccaaga    10200
gtatgctagc gatgagtcaa ttgtctttca acagcaataa gaaacgtatc actgactgca    10260
aagaaagagt agcctcaaac cgcaatcacg atcaaaagag caagaatcgt cggagagttg    10320
ccacttttat aacgactgac ctgcaaaagt actgtcttaa ttggagatat cagacaatca    10380
aactgttcgc tcatgccatc aatcagctga tgggcttacc tcacttcttc gaatggattc    10440
atctaagact aatggatact acgatgtttg taggagaccc tttcaatccc ccaagtgacc    10500
caactgactg tgatctctca agagtcccaa atgatgacat atatattgtc agtgctagag    10560
ggggtattga gggattatgt cagaagctat ggacaatgat ctcaattgct gcaatccaac    10620
ttgctgcagc aagatcacat tgtcgcgtcg cctgtatggt acagggtgac aatcaagtaa    10680
tagctgtaac gagagaggta aggtcagatg actccccgga aatggtgtta acacaattgc    10740
atcaagccag tgataatttc ttcaaggaat tgattcatgt taatcatttg attggccata    10800
atttgaagga tcgtgaaaca atcagatcag acacattctt catatacagc aaacgaatat    10860
tcaaagatgg agcaatactc agtcaagtcc tcaaaaattc atctaaatta gtgctaatat    10920
caggcgacct tagtgaaaac accgtaatgt cctgtgccaa cattgcatct actatagcac    10980
ggctgtgcga gaacgggctt ccaaaggatt tctgttatta cttaaactac ctgatgagtt    11040
gcgtgcagac atactttgat tctgagtttt ccatcactaa cagctcgcac cccgattcta    11100
accagtcgtg gattgaagac atctctttg tgcactcata tgtcctgacc cctgcccagc    11160 taggggact gagcaacctc caatactcaa ggctctacac gaggaacatc ggtgacccgg    11220
gaactactgc ttttgcagag atcaagcgat tagaagcagt ggggttacta agtcctagta    11280
ttatgactaa catcttaact aggccgcctg gaaatggaga ttgggccagt ctgtgtaacg    11340
acccttactc tttcaatttt gagactgtcg cgagtccaaa tattgtcctt aagaaacata    11400
cacaaagagt cctatttgaa acttgttcaa atccttatt atctggcgtg catacagagg    11460
ataatgaggc agaagagaag gcgttggctg aatttttact caatcaagaa gtaattcatc    11520
cacgtgtcgc acatgctatc atggaagcaa gctctatagg taggaggaag cagattcaag    11580
ggcttgttga cacaacaaac accgtaatca agattgcatt gactaggagg ccacttggca    11640
tcaagaggct gatgcggata gttaactact cgagcatgca tgcaatgctg tttagagacg    11700
atgttttctc atctaacagg tctaaccacc ccttagtttc ctctaatatg tgttctctga    11760
cgctagcaga ctatgcacgg aatagaagct ggtcaccatt gacgggggt agaaagatac    11820 tgggtgtatc taatcctgat actatagaac ttgtagaggg tgagatcctt agcgtcagcg    11880
gaggatgcaa aagatgtgac agcggagatg aacaattcac ttggttccat cttccgagca    11940
atatagaact gaccgatgac accagcaaga atcctccgat gagagtgccg tacctcgggt    12000
caaagactca agagaggagg gccgcctcgc ttgcgaaaat agctcatatg tcaccacatg    12060
tgaaagctgc tctaagggca tcatccgtgt tgatctgggc ttatggagac aacgaagtaa    12120
attggactgc tgctcttaaa attgcaagat ctcggtgcaa tataaactca gagtatcttc    12180
gactattgtc ccccttaccc acagctggga atctccaaca tagactggat gacggcataa    12240
ctcagatgac attcaccct gcatctctct acagggtgtc accttatatt cacatatcca    12300
atgattctca aggttattc acggaagaag gagtcaaaga gggaaatgta gtttatcagc    12360
aaatcatgct cttgggttta tctctaatcg aatcactctt cccgatgacg acaaccagga    12420
```

-continued

```
catacgatga gatcacattg cacctccaca gtaaatttag ctgctgtatc agggaagcac    12480
cggttgcagt tcctttcgag ttactcggga tggcaccaga actaaggaca gtgacctcaa    12540
ataagtttat gtatgatcct agtcctgtat cggagggtga cttttgcgaga cttgacttag   12600
ctatctttaa gagttatgag cttaatctag aatcatatcc cacaatagag ctaatgaaca    12660
ttctttcaat atccagcggg aagttaatcg gccagtctgt ggtttcttat gatgaagata    12720
cctccataaa gaatgacgcc ataatagtgt atgacaacac ccggaattgg atcagcgaag    12780
ctcagaattc agatgtggtc cgcctattcg agtatgcagc acttgaagtg cttctcgact    12840
gttcttatca gctctactat ctgagagtaa gaggcctaga caatatcgtg ttgtatatga    12900
gtgacttata taagaatatg ccaggaattc tactttccaa cattgcagct acaatatctc    12960
atcccatcat tcattcaaga ttgcatgcag taggcctggt caatcacgac gggtcacacc    13020
aacttgcaga cacagatttc atcgaaatgt ctgcaaaact attagtctct tgcactcgac    13080
gcgtggtctc aggtttatat gcagggaata agtatgatct gctgttcccg tctgtcttag    13140
atgataacct gagtgagaag atgcttcagc tgatatctcg gttatgctgc ctgtatacgg    13200
tgctctttgc tacaacaaga gagatcccga aaataagagg cttatctgca gaagagaagt    13260
gttcagtact tactgagtac ctactgtcag atgctgtgaa accattactt agttctgagc    13320
aagtgagctc tatcatgtct cctaacatag ttacgttccc agctaatcta tattacatgt    13380
ctcggaagag ccttaatttg attagggaaa gagaggacag ggacactatc ttggcattgt    13440
tgttcccccca agagccacta cttgagttcc ccttagtaca agatattggc gctcgagtga   13500
aagatccatt caccccgacaa cctgcggcgt ttttacaaga attagatttg agcgctccag   13560
caaggtatga cgcatttaca cttagtcagg ttcattctga acacacatca ccaaatccgg    13620
aggacgacta cttagtacga tacctgttca gaggaatagg gaccgcgtcc tcctcttggt    13680
ataaggcatc tcaccttctt tctgtacctg aggtcagatg tgcaaggcac gggaattcct    13740
tatacttggc agaaggaagc ggagccatta tgagtcttct cgaactgcat gtgccgcatg    13800
agactatcta ttacaatacg ctcttctcaa acgagatgaa ccccccacag cggcatttcg    13860
gaccgacccc aacacagttt ctgaattcag ttgtttatag gaatctacag gcggaggtac    13920
catgtaagga tggatttgtc caggagttcc gtccattatg gagagagaat acagaagaaa    13980
gcgatctgac ctcagataaa gcagtgggtt acatcacatc tgcagtgccc taccggtctg    14040
tatcattgct gcactgtgac attgagattc ctccaggatc caatcaaagc ttactggatc    14100
aactggctac caatctgtct ctgattgcca tgcattctgt aagggagggc ggggtcgtga    14160
tcatcaaagt gttgtatgca atgggatatt acttccatct actcatgaac ttgttcactc    14220
cgtgttctac gaaaggatat attctctcta atggctatgc atgtagaggg gatatggagt    14280
gttacctggt atttgtcatg ggctatcgag gtgggcctac atttgtacat gaggtagtga    14340
ggatggcaaa aactctagtg cagcggcacg gtacacttttt gtccaaatca gatgagatca   14400
cactgactag gttatttacc tcacagcggc agcgtgtaac agacatccta tccagtcctt    14460
taccgagact aataaagttc ttgagaaaga atatcgatac tgcgctaatt gaagccgggg    14520
gacaacccgt ccgtccattc tgtgcagaga gcttggtgag gacactagcg gacacaactc    14580
agatgaccca gatcatcgct agtcacattg acacagtcat tcgatctgtg atctacatgg    14640
aggctgaggg tgatctcgcc gacacagtgt tcttatttac ccctacaat ctctctacag     14700
acggtaaaaa gagaacatca cttaaacagt gcacaaggca gatcttagag gtcacaatat    14760
tgggtcttag agttgaaaat ctcaataaag taggtgatgt agtcagtcta gtacttaaag    14820
```

```
gtatgatttc tctggaggac ctgatccctc taagaacata cttgaagcgt agtacctgcc   14880
ctaagtattt gaagtctgtt ctaggtatta ctaaactcaa agaaatgttt acagacacct   14940
ctttattata cttgactcgt gctcaacaaa aattctacat gaaaactata ggcaacgcag   15000
tcaagggata ctacagtaac tgtgactctt aaagataatc acatattaat aggctccttt   15060
tctagttaac tgagcccttg ttgatttaat gatactatat tagaaaaaag ttgcactccg   15120
atcctttagg actcgtgttc gaattcaaat aattgtctta gaaaaaagtt gcgcgtaatt   15180
gttcttgaat gtagtcctgt cattcaccaa atctttgttt ggtcggcatg gcatctccac   15240
ctcctcgcgg tccgacctgg gcatccgaag gaggacgcac gtccactcgg atggctaagg   15300
gagtagcata acccttggg gcctctaaac gggtcttgag gggttttttg ggcgcgccgt   15360
cgaccgatgc ccttgagagc cttcaaccca gtcagctcct tccggtgggc gcggggcatg   15420
actatcgtcg ccgcacttat gactgtcttc tttatcatgc aactcgtagg acaggtgccg   15480
gcagcgctct gggtcatttt cggcgaggac cgctttcgct ggagcgcgac gatgatcggc   15540
ctgtcgcttg cggtattcgg aatcttgcac gccctcgctc aagccttcgt cactggtccc   15600
gccaccaaac gtttcggcga gaagcaggcc attatcgccg gcatggcggc cgacgcgctg   15660
ggctacgtct tgctggcgtt cgcgacgcga ggctggatgg ccttccccat tatgattctt   15720
ctcgcttccg gcggcatcgg gatgcccgcg ttgcaggcca tgctgtccag gcaggtagat   15780
gacgaccatc agggacagct tcaaggatcg ctcgcggctc ttaccagcct aacttcgatc   15840
actggaccgc tgatcgtcac ggcgatttat gccgcctcgg cgagcacatg gaacgggttg   15900
gcatggattg taggcgccgc cctataacctt gtctgcctcc ccgcgttgcg tcgcggtgca   15960
tggagccggg ccacctcgac ctgaatggaa gccggcggca cctcgctaac ggattcacca   16020
ctccaagaat tggagccaat caattcttgc ggagaactgt gaatgcgcaa accaacccctt   16080 ggcagaacat atccatcgcg tccgccatct ccagcagccg cacgcggcgc atctcgggca   16140
gcgttgggtc ctggccacgg gtgcgcatga tcgtgctcct gtcgttgagg acccggctag   16200
gctggcgggg ttgccttact ggttagcaga atgaatcacc gatacgcgag cgaacgtgaa   16260
gcgactgctg ctgcaaaacg tctgcgacct gagcaacaac atgaatggtc ttcggtttcc   16320
gtgtttcgta aagtctggaa acgcggaagt cagcgccctg caccattatg ttccggatct   16380
gcatcgcagg atgctgctgg ctaccctgtg gaacacctac atctgtatta acgaagcgct   16440
ggcattgacc ctgagtgatt tttctctggt cccgccgcat ccataccgcc agttgtttac   16500
cctcacaacg ttccagtaac cgggcatgtt catcatcagt aacccgtatc gtgagcatcc   16560
tctctcgttt catcggtatc attacccca tgaacagaaa tccccttac acggaggcat   16620 cagtgaccaa acaggaaaaa accgccctta acatggcccg ctttatcaga agccagacat   16680
taacgcttct ggagaaactc aacgagctgg acgcggatga acaggcagac atctgtgaat   16740
cgcttcacga ccacgctgat gagctttacc gcagctgcct cgcgcgtttc ggtgatgacg   16800
gtgaaaacct ctgacacatg cagctcccgg agacggtcac agcttgtctg taagcggatg   16860
ccgggagcag acaagcccgt cagggcgcgt cagcgggtgt tggcgggtgt cggggcgcag   16920
ccatgaccca gtcacgtagc gatagcggag tgtatactgg cttaactatg cggcatcaga   16980
gcagattgta ctgagagtgc accatatgcg gtgtgaaata ccgcacagat gcgtaaggag   17040
aaaataccgc atcaggcgct cttccgcttc ctcgctcact gactcgctgc gctcggtcgt   17100
tcggctgcgg cgagcggtat cagctcactc aaaggcggta atacggttat ccacagaatc   17160
```

```
agggggataac gcaggaaaga acatgtgagc aaaaggccag caaaaggcca ggaaccgtaa    17220
aaaggccgcg ttgctggcgt ttttccatag gctccgcccc cctgacgagc atcacaaaaa    17280
tcgacgctca agtcagaggt ggcgaaaccc gacaggacta taaagatacc aggcgtttcc    17340
ccctggaagc tccctcgtgc gctctcctgt tccgaccctg ccgcttaccg gatacctgtc    17400
cgcctttctc ccttcgggaa gcgtggcgct ttctcatagc tcacgctgta ggtatctcag    17460
ttcggtgtag gtcgttcgct ccaagctggg ctgtgtgcac gaaccccccg ttcagcccga    17520
ccgctgcgcc ttatccggta actatcgtct tgagtccaac ccggtaagac acgacttatc    17580
gccactggca gcagccactg gtaacaggat tagcagagcg aggtatgtag gcggtgctac    17640
agagttcttg aagtggtggc ctaactacgg ctacactaga aggacagtat ttggtatctg    17700
cgctctgctg aagccagtta ccttcggaaa aagagttggt agctcttgat ccggcaaaca    17760
aaccaccgct ggtagcggtg gttttttttgt ttgcaagcag cagattacgc gcagaaaaaa    17820
aggatctcaa gaagatcctt tgatcttttc tacgggtct gacgctcagt ggaacgaaaa    17880
ctcacgttaa gggattttgg tcatgagatt atcaaaaagg atcttcacct agatcctttt    17940
aaattaaaaa tgaagtttta atcaatcta aagtatatat gagtaaactt ggtctgacag    18000
ttaccaatgc ttaatcagtg aggcacctat ctcagcgatc tgtctatttc gttcatccat    18060
agttgcctga ctccccgtcg tgtagataac tacgatacgg gagggcttac catctggccc    18120
cagtgctgca atgataccgc gagacccacg ctcaccggct ccagatttat cagcaataaa    18180
ccagccagcc ggaagggccg agcgcagaag tggtcctgca actttatccg cctccatcca    18240
gtctattaat tgttgccggg aagctagagt aagtagttcg ccagttaata gtttgcgcaa    18300
cgttgttgcc attgctgcag gcatcgtggt gtcacgctcg tcgtttggta tggcttcatt    18360
cagctccggt tcccaacgat caaggcgagt tacatgatcc cccatgttgt gcaaaaaagc    18420
ggttagctcc ttcggtcctc cgatcgttgt cagaagtaag ttggccgcag tgttatcact    18480
catggttatg gcagcactgc ataattctct tactgtcatg ccatccgtaa gatgcttttc    18540
tgtgactggt gagtactcaa ccaagtcatt ctgagaatag tgtatgcggc gaccgagttg    18600
ctcttgcccg gcgtcaacac gggataatac cgcgccacat agcagaactt taaaagtgct    18660
catcattgga aaacgttctt cggggcgaaa actctcaagg atcttaccgc tgttgagatc    18720
cagttcgatg taacccactc gtgcacccaa ctgatcttca gcatctttta ctttcaccag    18780
cgtttctggg tgagcaaaaa caggaaggca aaatgccgca aaaaagggaa taagggcgac    18840
acggaaatgt tgaatactca tactcttcct ttttcaatat tattgaagca tttatcaggg    18900
ttattgtctc atgagcggat acatatttga atgtatttag aaaaataaac aaatagggggt    18960 tccgcgcaca tttccccgaa aagtgccacc tgacgtctaa gaaaccatta ttatcatgac    19020
attaacctat aaaaataggc gtatcacgag gccctttcgt cttcaagaat tctaatacga    19080
ctcactatag g                                                        19091
```

<210> SEQ ID NO 2
<211> LENGTH: 20314
<212> TYPE: DNA
<213> ORGANISM: Artificial Sequence
<220> FEATURE:
<223> OTHER INFORMATION: LVP-K1-PTEN

<400> SEQUENCE: 2

```
accaaacaga gaatccgtaa ggtacgatag aaggcgaagg agcaatcgaa gtcgtacggg      60
tagaaggtgt gaatctcgag tgcgagcccg aagctcaaac tcgagagagc cttctgccaa     120
```

```
aatgtcttct gtattcgatg agtacgagca gctcctcgcg gctcagactc gccccaatgg    180
agctcatggc ggaggagaga aggggagcac cttaaaggta gaagtcccgg tattcactct    240
caacagtgat gacccagaag atagatggaa ctttgcagtg ttttgtcttc ggattgctgt    300
tagcgaggat gccaacaaac cacttaggca aggtgctctc atatctctct tatgttccca    360
ctctcaagtg atgaggaacc atgttgccct tgcggggaaa cagaatgagg ccacactggc    420
tgttcttgag atcgatggtt ttaccaacgg cgtgccccag ttcaacaaca ggagtggagt    480
gtctgaagag agagcacaga gatttatgat gatagcaggg tctctccctc gggcatgcag    540
caacggtacc ccgttcgtca cagctggggt tgaagatgat gcaccagaag acattactga    600
taccctggag aggatcctct ctatccaggc tcaagtatgg gtcacggtgg caaaggccat    660
gactgcatat gagacagcag atgagtcaga acaagaaga atcaataagt acatgcagca    720
aggcagggtc cagaagaagt acatcctcca ccccgtatgc aggagcgcaa tccaactcac    780
aatcagacag tctctggcgg tccgcatctt tttggttagc gagcttaaga gaggccgcaa    840
cacggcaggt gggacctcca cctattacaa cttggtgggg gatgtagact catacatcag    900
gaacactggg ctaactgcat tcttcctgac acttaaatat ggaattaaca ccaagacatc    960
agcccttgca cttagcagcc tctcaggcga tatccagaaa atgaagcagc tcatgcgctt   1020
gtatcggatg aaaggagata atgcgccgta catgacattg ctcggtgaca gtgaccagat   1080
gagctttgca cctgccgagt atgcacaact ttactccttt gccatgggta tggcatcagt   1140
cctagataaa ggaactagca aataccaatt tgccagggac tttatgagca catcattctg   1200
gagacttgga gtagagtacg ctcaggctca aggaagtagc atcaatgagg atatggccgc   1260
cgagctaaag ctaaccccag cagcaaggag aggcctggca gctgctgccc aaagagtgtc   1320
tgaggagacc agcagcatgg acatgcccac ccaacaagcc ggggtcctca ctggactcag   1380
cgacggaggc tcccaagccc ccaaggtgc actgaacaga tcacaaggc aaccggacac   1440 cggggatggg gagacccaat ttctggatct gatgagagcg gtggcaaata gcatgagaga   1500
agcgccaaac tctgcgcagg gcaccccctca accggggcct cccccaaccc ctgggccctc   1560
tcaagacaat gacaccgact gggggtactg accgacagca cccagtttgc ttctatgagg   1620
tcatcccaat tcctctgctt agaaaaaata cgggtagaag cggccgcggc cggccaccat   1680
gacagccatc atcaaagaga tcgttagcag aaacaaaagg agatatcaag aggatggatt   1740
cgacttagac ttgacctata tttatccaaa cattattgct atgggatttc ctgcagaaag   1800
acttgaaggc gtatacagga acaatattga tgatgtagta aggttttgg attcaaagca   1860 taaaaaccat tacaagatat acaatctttg tgctgaaaga cattatgaca ccgccaaatt   1920
taattgcaga gttgcacaat atccttttga agaccataac ccaccacagc tagaacttat   1980
caaacccttt tgtgaagatc ttgaccaatg gctaagtgaa gatgacaatc atgttgcagc   2040
aattcactgt aaagctggaa agggacgaac tggtgtaatg atatgtgcat atttattaca   2100
tcggggcaaa ttttaaagg cacaagaggc cctagatttc tatgggaag taaggaccag   2160 agacaaaaag ggagtaacta ttcccagtca gaggcgctat gtgtattatt atagctacct   2220
gttaaagaat catctggatt atagaccagt ggcactgttg tttcacaaga tgatgtttga   2280
aactattcca atgttcagtg gcggaacttg caatcctcag tttgtggtct gccagctaaa   2340
ggtgaagata tattcctcca attcaggacc cacacgacgg gaagacaagt tcatgtactt   2400
tgagttccct cagccgttac ctgtgtgtgg tgatatcaaa gtagagttct tccacaaaca   2460
```

```
gaacaagatg ctaaaaaagg acaaaatgtt tcacttttgg gtaaatacat tcttcatacc    2520
aggaccagag gaaacctcag aaaaagtaga aaatggaagt ctatgtgatc aagaaatcga    2580
tagcatttgc agtatagagc gtgcagataa tgacaaggaa tatctagtac ttactttaac    2640
aaaaaatgat cttgacaaag caaataaaga caaagccaac cgatactttt ctccaaattt    2700
taaggtgaag ctgtacttca caaaaacagt agaggagccg tcaaatccag aggctagcag    2760
ttcaacttct gtaacaccag atgttagtga caatgaacct gatcattata gatattctga    2820
caccactgac tctgatccag agaatgaacc ttttgatgaa gatcagcata cacaaattac    2880
aaaagtctga ggccggcccc acaccccacc cctcaatccg caatcccgca tggccaaacc    2940
cacaaacgaa ccccctgtc tccctcctct ccccagccc cacaacccca cctgcccagg    3000
gcaacatagg tacaatgcga cccactaata atcaatacag ggccaaagaa attagaaaaa    3060
agtacgggta gaagggagac attcagagat cagggcgagt caccccgggtc tctgctctcc    3120 cttctaccta gtggattagg atggagatgg ccacctttac agatgcggag atcgacgagc    3180
tatttgagac cagtggaact gtcattgaca gcataattac ggcccaggga aaaccagtag    3240
agactgttgg aaggagtgca atcccacaag gcaaaactaa ggctttgagc gcagcatggg    3300
agaagcatgg gagcatccag tcaccagcca gccaagacac ccctgatcga caggacagat    3360
cagataaaca actgtccaca cccgagcaag cgagtccaaa cgacagcccc ccagccacat    3420
ccactgacca gcctcccact caggctgcag atgaggccgg cgatacacag ctcaagaccg    3480
gagcaagcaa ctctctgctg tcgatgcttg ataaactcag caataagtca tctaatgcta    3540 aaagggccc agggtcgagc cctcaagaaa ggcatcatca acgtctgact caacaacagg    3600
ggagtcaaca aagccgcgga aacagccaag agagaccgca gaaccaggcc aaggccatcc    3660
ctggaaacca ggtcacagac gcgaacacag catatcatgg acaatgggag gagtcacaac    3720
tatcagctgg tgcaacccat catgctctcc gatcagagca gagccaagac aatactcctg    3780
cacctgtgga tcatgtccag ctacctgtcg actttgtgca ggcgatgatg tctatgatgg    3840
aggcgatatc acagagggta agtaaagttg actatcagct ggaccttgtc ttgaaacaga    3900
catcttctat ccccatgatg cggtctgaaa tccagcagct gaaaacgtct gttgcggtca    3960
tggaagccaa tttgggcatg atgaagatcc tggaccctgg ttgtgccaac gtttcatctc    4020
taagtgatct acgggcagtt gcccgatccc acccggtttt aatttctggc cccgagacc    4080 catctcctta tgtgacccaa gggggcgaaa tggcactcaa taaactttcg caaccggtgc    4140
aacacccctc tgaattgatt aaacccgcca cggcaagcgg gcctgatata ggagtggaga    4200
aagacactgt ccgtgcattg atcatgtcac gccctatgca tccgagctct tcagctaggc    4260
tcttgagcaa actggacgca gccggatcga ttgaggaaat cagaaaaatc aagcgccttg    4320
cactgaatgg ctaatcacca ccgcaacccg cagcagatcc ctgtccaccc agcaccacac    4380
ggtatctgca ccaagctcct ctctgcaaac ccaaggtcca acaccccgag cgacaaccct    4440
gtcctgcttc ctctgcccca ctaaatgatc gcgcagctgc aatcaattca gctatattaa    4500
ggattaagaa aaaatacggg tagaatcgga gtgccccgat tgtgccaaga tggactcatc    4560
taggacaatc gggctgtact ttgattctac ccttccttct agcaacctgc tagcattccc    4620
gatagtccta caagacacag gggacgggaa gaagcaaatc gccccgcaat acaggatcca    4680
gcgtcttgac tcgtggacag acagcaaaga agactcggta ttcatcacca cctatggatt    4740
catctttcag gttgggaatg aagaagccac tgtcggcatg atcaatgata atcccaagcg    4800
cgagttactt tccactgcca tgctatgcct agggagtgta ccaaatgtcg gagatcttgt    4860
```

| | |
|---|---|
| tgagctggca agggcctgcc tcactatggt ggtaacatgc aagaagagtg caactaacac | 4920 |
| cgagagaatg gtcttctcag tagtgcaggc accccaggtg ctgcaaagct gtagggttgt | 4980 |
| ggcaaacaaa tactcgtcgg tgaatgcagt caagcacgtg aaagcaccag agaagattcc | 5040 |
| tgggagcgga accctagagt acaaagtgaa ctttgtctct ctgaccgtgg tgccaagaaa | 5100 |
| ggacgtctac aagataccaa ctgcagcact taaggtctct ggctcaagtc tgtacaatct | 5160 |
| tgcgctcaat gtcactattg atgtggaggt agacccgaag agcccgttgg tcaaatccct | 5220 |
| ttccaagtcc gacagtgggt actatgctaa tctcttctta catattgggc ttatgtccac | 5280 |
| tgtagataag aagggggaaga aagtgacatt tgacaagctg gaaaggaaga taaggagact | 5340 |
| tgatctatct gtagggctta gtgacgtgct cggaccttcc gtgcttgtaa aggcgagagg | 5400 |
| tgcacggact aagctgctgg caccttttctt ctctagcagt gggacagcct gctatcccat | 5460 |
| agcaaatgcc tctcctcagg tggccaagat actctggagc caaaccgcgt acctgcggag | 5520 |
| tgtaaaagtc attatccaag cgggcaccca gcgtgctgtc gcagtgaccg ccgaccacga | 5580 |
| ggttacctct actaagctgg agaaggggca taccattgcc aaatacaatc ccttcaagaa | 5640 |
| ataggctgca tctctgagat tgcactccgc ccatcttccc ggatcaccat gacactaaat | 5700 |
| aatgatctgt cttgattact tatagttagt tcgcctgtct atcaaattag aaaaaacacg | 5760 |
| ggtagaagat tctggatccc ggttggcgcc ttcaaggtgc aagatgggct ccagatcttc | 5820 |
| taccaggatc ccagtacctc ttatgctgac cgtccgagtc atgttggcac tgagttgcgt | 5880 |
| ctgtccgacc agcgcccttg atggcaggcc tcttgcagct gcagggattg tggtaacagg | 5940 |
| agacaaagca gtcaacatat acacctcatc tcagacaggg tcaatcataa tcaagttact | 6000 |
| cccaaatatg cccaaggata aagaggcgtg tgcaaaagcc ccgttggagg catcaacag | 6060 |
| gacattgact actttgctca ccccccttgg tgattctatc cgtaggatac aagagtctgt | 6120 |
| gaccacgtcc ggaggaggga acagggacg tcttataggc gccattatcg gtggtgtagc | 6180 |
| tctcggggtt gcaaccgctg cacagataac agcagcctcg gctctgatac aagccaatca | 6240 |
| aaatgctgcc aacatactcc ggctaaaaga gagcattgct gcaaccaatg aggctgtgca | 6300 |
| cgaggtcact aatggattat cacaactagc agtggcagtt gggaagatgc agcaatttgt | 6360 |
| taatgaccag tttaataaaa cagctcagga attggactgt ataaaaatta cacagcaggt | 6420 |
| tggtgtagaa ctcaacctgt acctaactga attgactaca gtattcgggc cacaaatcac | 6480 |
| ttcccctgcc ttaactcagc tgactatcca ggcgctttac aatctagctg gtgggaatat | 6540 |
| ggattacttg ttgactaagt taggtgtggg gaacaaccaa ctcagctcat taattagtag | 6600 |
| tggcctgatc accggcaacc ctattctgta cgactcacag actcaactct ggggtataca | 6660 |
| ggtaacccta ccctcagtcg ggaacctaaa taatatgcgt gccacctacc tggaaacctt | 6720 |
| gtctgtaagt acaaccaaag gatttgcctc agcacttgtc ccaaaagtag tgacacaggt | 6780 |
| cggttccgtg atagaagagc ttgacacctc gtactgtata gagaccgatt tggatctata | 6840 |
| ttgtacaaga atagtgacat tccctatgtc tcctggtatt tattcctgtt tgagtggcaa | 6900 |
| tacatctgct tgcatgtact caaagactga aggcgcactc actacgccgt atatgacct | 6960 |
| caaaggctca gttattgcta actgtaagat gacaacatgt agatgtgcag accccccggg | 7020 |
| tatcatatcg caaaattatg gagaagctgt gtctctaata gataggcaat catgcaatat | 7080 |
| cttatcctta gacgggataa ctttgaggct cagtggggaa tttgatgcaa cttatcaaaa | 7140 |
| gaatatctca atacaagatt ctcaagtaat agtgacaggc aatcttgata tctcgactga | 7200 |

```
gcttgggaat gtcaacaact cgataagtaa tgctttggat aagttagagg aaagcaacag    7260
caaactagat aaggtcaatg tcaaactgac cagcacatcc gctcttatta cctatatcgt    7320
tttaactgtc atatctcttg tatgtggtat acttagcctg gttctagcat gctacctgat    7380
gtacaagcaa aaggcgcaac agaagacctt gttgtggctt gggaataata ccctagacca    7440
gatgagggcc actacaaaaa tgtgaatgcg gatgagaggc agaaacatcc ccaatagcag    7500
tttgtgtgta aagtctgaca gcctgttaat tagaagaatt aagaaaaaac taccggatgt    7560
agatgaccaa agggcgatat acgggtagaa cggtcgggga ggccgtccct caatcgggag    7620
ccgggcctca caacatccgt tctaccgcat caccaatagc agttttcagt catggaccgc    7680
gcagttagcc aagttgcgct agagaatgat gaaagagagg caaagaatac atggcgcttg    7740
gtattccgga tcgcaatcct actctcaacg gtggtgacct tagccatctc tgcagccgcc    7800
cttgcatata gcatggaggc cagcacacct agcgatcttg taggcatacc gactgcgatc    7860
tctagagcag aggaaaagat tacatctgca ctcggttcca atcaagatgt agtagatagg    7920
atatataagc aggtggccct cgaatctcca ctggcattgc taaacaccga atctacaatt    7980
atgaacgcaa taacgtctct ctcttatcga atcaatgggg ccgcaaatag cagcggatgt    8040
ggagcaccca ttcatgatcc agattatatt ggaggaatag gtaaagaact tattgtagat    8100
gatgctagcg acgtcacatc atactatccc tctgcgttcc aagaacacct gaactttatc    8160
ccggcgccta ctacaggatc aggttgcact cggatacect catttgacat gagcgctacc    8220
cactactgtt atactcacaa tgtgatatta tctggctgca gagatcactc gcactcacat    8280
caatatttag cacttggtgt gcttcggaca tctgcaacag ggagggtatt cttttccact    8340
ctgcgttcca tcaatctgga tgacacccaa aatcggaagt cttgcagtgt gagtgcaacc    8400
cccttgggtt gtgatatgct gtgctctaaa gtcacagaga ctgaagaaga ggattataac    8460
tcagctatcc ccacgtcgat ggtacatgga aggttagggt tcgacggcca ataccacgag    8520
aaggacctag atgtcacaac actattcgag gactgggtgg caaactaccc aggagtaggg    8580
ggcgggtctt ttattgacaa ccgcgtatgg ttcccagttt acggagggct aaaacccaat    8640
tcgcccagtg acaccgcaca agaagggaaa tatgtaatat acaagcgata caatgacaca    8700
tgtccagatg agcaagatta tcagattcaa atggctaagt cttcatataa gcctgggcgg    8760
tttggaggga aacgcgtaca gcaggccatc ttatctatca aagtgtcaac atccttgggc    8820
gaggacccgg tactgactgt accgcccaac acagtaacac tcatggggc cgaaggcaga    8880 gttctcacag tagggacatc tcatttcctt tatcagcgag ggtcatcata cttctcccct    8940
gccctactat atcctatgat agtcagcaac aaaacagcca ctcttcatag tccttataca    9000
ttcaatgcct tcactcgacc aggtagtgtc ccttgccagg cttcagcaag atgccctaac    9060
tcatgtgtta ccggagtcta tactgatcca tatcccttgg tcttctatag gaaccacacc    9120
ttgcgagggg tattcgggac gatgcttgat gataaacaag caagactcaa ccctgtatct    9180
gcagtatttg acagcatatc ccgcagtcgc ataacccggg tgagttcaag cagcaccaag    9240
gcagcataca caacatcaac atgttttaaa gttgtaaaga ccaataaaac ctattgtctc    9300
agcattgccg aaatatccaa taccctcttc ggggaattca gaatcgtccc tttactagtt    9360
gagattctca aggatgatgg ggttagagaa gccaggtcta gccggttgag tcaactgcga    9420
gagggttgga agatgacat tgtatccct atcttttgcg acgccaagaa tcaaactgaa    9480
taccggcgcg agctcgagtc ctacgctgcc agttggccat aatcagctag tgctaatgtg    9540
attagattaa gtcttgtcgg tagtcacttg attaagaaaa aatgtgggtg gtagcgggat    9600
```

```
ataaggcaaa acaactcaag gaggatagca cgggtaggac atggcgagct ccggtcccga    9660
gagggcggag catcagatta tcctaccaga gtcacacctg tcttcaccat tagtcaagca    9720
caaactactc tattactgga aattaactgg gctaccactc cctgacgagt gtgacttcga    9780
ccacctcatt ctcagccgac aatggaagaa aatacttgaa tcggcctccc ctgacactga    9840
gagaatgata aaacttggaa gggcagtgca ccagactctc aaccacaatt ccaagataac    9900
cggagtactc catcccaggt gtttagaaga attggctagt attgaggttc ctgactcaac    9960
caacaagttt cggaagatcg agaagaaaat ccaaattcac aacacaaggt atggagaact   10020
gttcacaaga ctgtgcacgc atgtagagaa gaaattgttg ggatcatctt ggtctaataa   10080
tgtcccccgg tcagaagagt tcaacagcat ccgtacagat ccggcattct ggtttcactc   10140
aaaatggtcc acaactaagt ttgcatggct ccatataaaa cagattcaaa ggcatctgat   10200
tgtggcagca agaacaaggt ccgcagccaa caaattggtg acgctgaccc ataaggtagg   10260
ccaagtcttt gttactcctg agcttgtcat tgtgacacat acagatgaga acaagttcac   10320
gtgtcttacc caggaacttg tgttgatgta tgcagatatg atggagggca gagatatggt   10380
caacataata tcatccacgg cggcacatct caggagccta tcagagaaaa ttgatgacat   10440
tctgcggtta gtagatgccc tggcaaaaga tctgggtaat caagtctacg atgttgtagc   10500
actcatggag ggatttgcat acggcgccgt ccagctgctt gagccgtcag gtacattcgc   10560
aggggatttc ttcgcattca acctgcagga gctcaaagac actttgatcg gcctccttcc   10620
taaggatata gcagaatctg tgactcacgc aatagccact gtattctctg cttagaaca   10680 aaatcaagcg gctgagatgc tgtgcctgtt gcgtctatgg ggccacccat tacttgagtc   10740
ccgtattgcg gcaaaagcag taaggagcca aatgtgcgca ccaaaaatgg tagactttga   10800
tatgatcctc caggtattgt ctttctttaa aggaacaatc atcaacggat acagaaagaa   10860
gaatgcaggt gtttggccac gtgtcaaagt agatacgata tacgggaagg tcattgggca   10920
gctacacgct gattcagcgg agatttcaca cgatatcatg ttgagagagt acaagagttt   10980
atctgcgctt gaattcgagc catgtataga atacgaccct atcaccaatc tgagcatgtt   11040
tctaaaagac aaggcgatcg cacacccgaa agacaactgg ctcgccgcgt ttaggcgaaa   11100
ccttctctct gaggaccaga agaaacatgt aaaggaggca acctctacta accgtctctt   11160
gatagagttc ttagagtcaa atgattttga tccatataag gagatggaat atctgacgac   11220
ccttgagtac ctaagagatg acaatgtggc agtatcatac tcgctcaagg agaaggaagt   11280
gaaggttaat gggcggattt ttgctaagct aacaaagaaa ttaaggaact gtcaagtgat   11340
ggcggaaggg atcttagctg accagattgc acctttcttt caagggaatg gggtcattca   11400
ggatagcata tctttaacca agagtatgct agcgatgagt caattgtctt tcaacagcaa   11460
taagaaacgt atcactgact gcaaagaaag agtagcctca aaccgcaatc acgatcaaaa   11520
gagcaagaat cgtcggagag ttgccacttt tataacgact gacctgcaaa agtactgtct   11580
taattggaga tatcagacaa tcaaactgtt cgctcatgcc atcaatcagc tgatgggctt   11640
acctcacttc ttcgaatgga ttcatctaag actaatggat actacgatgt tgtaggaga    11700 cccttttcaat cccccaagtg acccaactga ctgtgatctc tcaagagtcc caatgatga   11760 catatatatt gtcagtgcta gaggggggtat tgagggatta tgtcagaagc tatggacaat   11820
gatctcaatt gctgcaatcc aacttgctgc agcaagatca cattgtcgcg tcgcctgtat   11880
ggtacagggt gacaatcaag taatagctgt aacgagagag gtaaggtcag atgactcccc   11940
```

```
ggaaatggtg ttaacacaat tgcatcaagc cagtgataat ttcttcaagg aattgattca   12000
tgttaatcat ttgattggcc ataatttgaa ggatcgtgaa acaatcagat cagacacatt   12060
cttcatatac agcaaacgaa tattcaaaga tggagcaata ctcagtcaag tcctcaaaaa   12120
ttcatctaaa ttagtgctaa tatcaggcga ccttagtgaa aacaccgtaa tgtcctgtgc   12180
caacattgca tctactatag cacggctgtg cgagaacggg cttccaaagg atttctgtta   12240
ttacttaaac tacctgatga gttgcgtgca gacatacttt gattctgagt tttccatcac   12300
taacagctcg caccccgatt ctaaccagtc gtggattgaa gacatctctt ttgtgcactc   12360
atatgtcctg acccctgccc agctaggggg actgagcaac ctccaatact caaggctcta   12420
cacgaggaac atcggtgacc cgggaactac tgcttttgca gagatcaagc gattagaagc   12480
agtggggtta ctaagtccta gtattatgac taacatctta actaggccgc ctggaaatgg   12540
agattgggcc agtctgtgta acgacccctt actctttcaat tttgagactg tcgcgagtcc   12600
aaatattgtc cttaagaaac atacacaaag agtcctattt gaaacttgtt caaatccctt   12660
attatctggc gtgcatacag aggataatga ggcagaagag aaggcgttgg ctgaattttt   12720
actcaatcaa gaagtaattc atccacgtgt cgcacatgct atcatggaag caagctctat   12780
aggtaggagg aagcagattc aagggcttgt tgacacaaca aacaccgtaa tcaagattgc   12840
attgactagg aggccacttg gcatcaagag gctgatgcgg atagttaact actcgagcat   12900
gcatgcaatg ctgtttagag acgatgtttt ctcatctaac aggtctaacc ccccttagt   12960 ttcctctaat atgtgttctc tgacgctagc agactatgca cggaatagaa gctggtcacc   13020
attgacgggg ggtagaaaga tactgggtgt atctaatcct gatactatag aacttgtaga   13080
gggtgagatc cttagcgtca gcggaggatg cacaagatgt gacagcggag atgaacaatt   13140
cacttggttc catcttccga gcaatataga actgaccgat gacaccagca gaatcctcc   13200 gatgagagtg ccgtacctcg ggtcaaagac tcaagagagg agggccgcct cgcttgcgaa   13260
aatagctcat atgtcaccac atgtgaaagc tgctctaagg gcatcatccg tgttgatctg   13320
ggcttatgga gacaacgaag taaattggac tgctgctctt aaaattgcaa gatctcggtg   13380
caatataaac tcagagtatc ttcgactatt gtccccctta cccacagctg gaatctcca   13440 acatagactg gatgacggca taactcagat gacattcacc cctgcatctc tctacagggt   13500
gtcaccttat attcacatat ccaatgattc tcaaaggtta ttcacggaag aaggagtcaa   13560
agagggaaat gtagtttatc agcaaatcat gctcttgggt ttatctctaa tcgaatcact   13620
cttcccgatg acgacaacca ggacatacga tgagatcaca ttgcacctcc acagtaaatt   13680
tagctgctgt atcagggaag caccggttgc agttcctttc gagttactcg ggatggcacc   13740
agaactaagg acagtgacct caaataagtt tatgtatgat cctagtcctg tatcggaggg   13800
tgactttgcg agacttgact tagctatctt taagagttat gagcttaatc tagaatcata   13860
tcccacaata gagctaatga acattctttc aatatccagc gggaagttaa tcggccagtc   13920
tgtggtttct tatgatgaag atacctccat aaagaatgac gccataatag tgtatgacaa   13980
cacccggaat tggatcagcg aagctcagaa ttcagatgtg tccgcctat tcgagtatgc   14040 agcacttgaa gtgcttctcg actgttctta tcagctctac tatctgagag taagaggcct   14100
agacaatatc gtgttgtata tgagtgactt atataagaat atgccaggaa ttctactttc   14160
caacattgca gctacaatat ctcatccat cattcattca agattgcatg cagtaggcct   14220
ggtcaatcac gacgggtcac accaacttgc agacacagat ttcatcgaaa tgtctgcaaa   14280
actattagtc tcttgcactc gacgcgtggt ctcaggttta tatgcaggga taagtatga   14340
```

```
tctgctgttc ccgtctgtct tagatgataa cctgagtgag aagatgcttc agctgatatc   14400
tcggttatgc tgcctgtata cggtgctctt tgctacaaca agagagatcc cgaaaataag   14460
aggcttatct gcagaagaga agtgttcagt acttactgag tacctactgt cagatgctgt   14520
gaaaccatta cttagttctg agcaagtgag ctctatcatg tctcctaaca tagttacgtt   14580
cccagctaat ctatattaca tgtctcggaa gagccttaat ttgattaggg aaagagagga   14640
cagggacact atcttggcat tgttgttccc ccaagagcca ctacttgagt tcccttagt    14700 acaagatatt ggcgctcgag tgaaagatcc attcacccga caacctgcgg cgttttaca    14760 agaattagat ttgagcgctc cagcaaggta tgacgcattt acacttagtc aggttcattc   14820
tgaacacaca tcaccaaatc cggaggacga ctacttagta cgatacctgt tcagaggaat   14880
agggaccgcg tcctcctctt ggtataaggc atctcacctt ctttctgtac ctgaggtcag   14940
atgtgcaagg cacgggaatt ccttatactt ggcagaagga agcggagcca ttatgagtct   15000
tctcgaactg catgtgccgc atgagactat ctattacaat acgctcttct caaacgagat   15060 gaaccccca cagcggcatt tcggaccgac cccaacacag tttctgaatt cagttgttta    15120
taggaatcta caggcggagg taccatgtaa ggatggattt gtccaggagt tccgtccatt   15180
atggagagag aatacagaag aaagcgatct gacctcagat aaagcagtgg gttacatcac   15240
atctgcagtg ccctaccggt ctgtatcatt gctgcactgt gacattgaga ttcctccagg   15300
atccaatcaa agcttactgg atcaactggc taccaatctg tctctgattg ccatgcattc   15360
tgtaagggag ggcggggtcg tgatcatcaa agtgttgtat gcaatgggat attacttcca   15420
tctactcatg aacttgttca ctccgtgttc tacgaaagga tatattctct ctaatggcta   15480
tgcatgtaga ggggatatgg agtgttacct ggtatttgtc atgggctatc gaggtgggcc   15540
tacatttgta catgaggtag tgaggatggc aaaaactcta gtgcagcggc acggtacact   15600
tttgtccaaa tcagatgaga tcacactgac taggttattt acctcacagc ggcagcgtgt   15660
aacagacatc ctatccagtc ctttaccgag actaataaag ttcttgagaa agaatatcga   15720
tactgcgcta attgaagccg ggggacaacc cgtccgtcca ttctgtgcag agagcttggt   15780
gaggacacta gcggacacaa ctcagatgac ccagatcatc gctagtcaca ttgacacagt   15840
cattcgatct gtgatctaca tggaggctga gggtgatctc gccgacacag tgttcttatt   15900 tacccctac aatctctcta cagacggtaa aaagagaaca tcacttaaac agtgcacaag    15960
gcagatctta gaggtcacaa tattgggtct tagagttgaa aatctcaata agtaggtga    16020 tgtagtcagt ctagtactta aaggtatgat ttctctggag gacctgatcc ctctaagaac   16080
atacttgaag cgtagtacct gccctaagta tttgaagtct gttctaggta ttactaaact   16140
caaagaaatg tttacagaca cctctttatt atacttgact cgtgctcaac aaaaattcta   16200
catgaaaact ataggcaacg cagtcaaggg atactacagt aactgtgact cttaaagata   16260
atcacatatt aataggctcc ttttctagtt aactgagccc ttgttgattt aatgatacta   16320
tattagaaaa aagttgcact ccgatccttt aggactcgtg ttcgaattca ataattgtc    16380 ttagaaaaaa gttgcgcgta attgttcttg aatgtagtcc tgtcattcac caaatctttg   16440
tttggtcggc atggcatctc cacctcctcg cggtccgacc tggcatccg aaggaggacg    16500 cacgtccact cggatggcta agggagtagc ataaccccct ggggcctcta acgggtctt    16560 gaggggtttt ttgggcgcgc cgtcgaccga tgccctttgag agccttcaac ccagtcagct   16620
ccttccggtg ggcgcggggc atgactatcg tcgccgcact tatgactgtc ttctttatca   16680
```

```
tgcaactcgt aggacaggtg ccggcagcgc tctgggtcat tttcggcgag gaccgctttc    16740
gctggagcgc gacgatgatc ggcctgtcgc ttgcggtatt cggaatcttg cacgccctcg    16800
ctcaagcctt cgtcactggt cccgccacca aacgtttcgg cgagaagcag gccattatcg    16860
ccggcatggc ggccgacgcg ctgggctacg tcttgctggc gttcgcgacg cgaggctgga    16920
tggccttccc cattatgatt cttctcgctt ccggcggcat cgggatgccc gcgttgcagg    16980
ccatgctgtc caggcaggta gatgacgacc atcagggaca gcttcaagga tcgctcgcgg    17040
ctcttaccag cctaacttcg atcactggac cgctgatcgt cacggcgatt tatgccgcct    17100
cggcgagcac atggaacggg ttggcatgga ttgtaggcgc cgccctatac cttgtctgcc    17160
tccccgcgtt gcgtcgcggt gcatggagcc gggccacctc gacctgaatg gaagccggcg    17220
gcacctcgct aacggattca ccactccaag aattggagcc aatcaattct gcggagaac     17280 tgtgaatgcg caaaccaacc cttggcagaa catatccatc gcgtccgcca tctccagcag    17340
ccgcacgcgg cgcatctcgg gcagcgttgg gtcctggcca cgggtgcgca tgatcgtgct    17400
cctgtcgttg aggacccggc taggctggcg gggttgcctt actggttagc agaatgaatc    17460
accgatacgc gagcgaacgt gaagcgactg ctgctgcaaa acgtctgcga cctgagcaac    17520
aacatgaatg gtcttcggtt ccgtgtttc  gtaaagtctg gaaacgcgga agtcagcgcc    17580
ctgcaccatt atgttccgga tctgcatcgc aggatgctgc tggctaccct gtggaacacc    17640
tacatctgta ttaacgaagc gctggcattg accctgagtg attttttctct ggtcccgccg    17700 catccatacc gccagttgtt taccctcaca acgttccagt aaccgggcat gttcatcatc    17760
agtaacccgt atcgtgagca tcctctctcg tttcatcggt atcattaccc ccatgaacag    17820
aaatccccct tacacggagg catcagtgac caaacaggaa aaaaccgccc ttaacatggc    17880
ccgctttatc agaagccaga cattaacgct tctggagaaa ctcaacgagc tggacgcgga    17940
tgaacaggca gacatctgtg aatcgcttca cgaccacgct gatgagcttt accgcagctg    18000
cctcgcgcgt ttcggtgatg acggtgaaaa cctctgacac atgcagctcc cggagacggt    18060
cacagcttgt ctgtaagcgg atgccgggag cagacaagcc cgtcagggcg cgtcagcggg    18120
tgttggcggg tgtcggggcg cagccatgac ccagtcacgt agcgatagcg gagtgtatac    18180
tggcttaact atgcggcatc agagcagatt gtactgagag tgcaccatat gcggtgtgaa    18240
ataccgcaca gatgcgtaag gagaaaatac cgcatcaggc gctcttccgc ttcctcgctc    18300
actgactcgc tgcgctcggt cgttcggctg cggcgagcgg tatcagctca ctcaaaggcg    18360
gtaatacggt tatccacaga atcagggggat aacgcaggaa agaacatgtg agcaaaaggc    18420
cagcaaaagg ccaggaaccg taaaaaggcc gcgttgctgg cgttttttcca taggctccgc    18480 cccccctgacg agcatcacaa aaatcgacgc tcaagtcaga ggtggcgaaa cccgacagga    18540
ctataaagat accaggcgtt tccccctgga agctccctcg tgcgctctcc tgttccgacc    18600
ctgccgctta ccggatacct gtccgccttt ctcccttcgg gaagcgtggc gctttctcat    18660
agctcacgct gtaggtatct cagttcggtg taggtcgttc gctccaagct gggctgtgtg    18720
cacgaacccc ccgttcagcc cgaccgctgc gccttatccg gtaactatcg tcttgagtcc    18780
aacccggtaa gacacgactt atcgccactg gcagcagcca ctggtaacag gattagcaga    18840
gcgaggtatg taggcggtgc tacagagttc ttgaagtggt ggcctaacta cggctacact    18900
agaaggacag tatttggtat ctgcgctctg ctgaagccag ttaccttcgg aaaaagagtt    18960
ggtagctctt gatccggcaa acaaaccacc gctggtagcg gtggtttttt tgtttgcaag    19020
cagcagatta cgcgcagaaa aaaaggatct caagaagatc ctttgatctt ttctacgggg    19080
```

```
tctgacgctc agtggaacga aaactcacgt taagggattt tggtcatgag attatcaaaa      19140
aggatcttca cctagatcct tttaaattaa aaatgaagtt ttaaatcaat ctaaagtata      19200
tatgagtaaa cttggtctga cagttaccaa tgcttaatca gtgaggcacc tatctcagcg      19260
atctgtctat ttcgttcatc catagttgcc tgactccccg tcgtgtagat aactacgata      19320
cgggagggct taccatctgg ccccagtgct gcaatgatac cgcgagaccc acgctcaccg      19380
gctccagatt tatcagcaat aaaccagcca gccggaaggg ccgagcgcag aagtggtcct      19440
gcaactttat ccgcctccat ccagtctatt aattgttgcc gggaagctag agtaagtagt      19500
tcgccagtta atagtttgcg caacgttgtt gccattgctg caggcatcgt ggtgtcacgc      19560
tcgtcgtttg gtatggcttc attcagctcc ggttcccaac gatcaaggcg agttacatga      19620
tcccccatgt tgtgcaaaaa agcggttagc tccttcggtc ctccgatcgt tgtcagaagt      19680
aagttggccg cagtgttatc actcatggtt atggcagcac tgcataattc tcttactgtc      19740
atgccatccg taagatgctt ttctgtgact ggtgagtact caaccaagtc attctgagaa      19800
tagtgtatgc ggcgaccgag ttgctcttgc ccggcgtcaa cacgggataa taccgcgcca      19860
catagcagaa ctttaaaagt gctcatcatt ggaaaacgtt cttcggggcg aaaactctca      19920
aggatcttac cgctgttgag atccagttcg atgtaaccca ctcgtgcacc caactgatct      19980
tcagcatctt ttactttcac cagcgtttct gggtgagcaa aaacaggaag gcaaaatgcc      20040
gcaaaaaagg gaataagggc gacacggaaa tgttgaatac tcatactctt cctttttcaa      20100
tattattgaa gcatttatca gggttattgt ctcatgagcg gatacatatt tgaatgtatt      20160
tagaaaaata aacaaatagg ggttccgcgc acatttcccc gaaaagtgcc acctgacgtc      20220
taagaaacca ttattatcat gacattaacc tataaaaata ggcgtatcac gaggcccttt      20280
cgtcttcaag aattctaata cgactcacta tagg                                 20314
```

<210> SEQ ID NO 3
<211> LENGTH: 1212
<212> TYPE: DNA
<213> ORGANISM: Artificial Sequence
<220> FEATURE:
<223> OTHER INFORMATION: PTEN

<400> SEQUENCE: 3

```
atgacagcca tcatcaaaga gatcgttagc agaaacaaaa ggagatatca agaggatgga       60
ttcgacttag acttgaccta tatttatcca aacattattg ctatgggatt tcctgcagaa      120
agacttgaag gcgtatacag gaacaatatt gatgatgtag taaggttttt ggattcaaag      180
cataaaaacc attacaagat atacaatctt tgtgctgaaa gacattatga caccgccaaa      240
tttaattgca gagttgcaca atatcctttt gaagaccata cccaccaca gctagaactt      300 atcaaaccct tttgtgaaga tcttgaccaa tggctaagtg aagatgacaa tcatgttgca      360
gcaattcact gtaaagctgg aaagggacga actggtgtaa tgatatgtgc atatttatta      420
catcggggca aatttttaaa ggcacaagag gccctagatt tctatgggga agtaaggacc      480
agagacaaaa agggagtaac tattcccagt cagaggcgct atgtgtatta ttatagctac      540
ctgttaaaga atcatctgga ttatagacca gtggcactgt tgtttcacaa gatgatgttt      600
gaaactattc caatgttcag tggcggaact tgcaatcctc agtttgtggt ctgccagcta      660
aaggtgaaga tatattcctc caattcagga cccacacgac gggaagacaa gttcatgtac      720
tttgagttcc ctcagccgtt acctgtgtgt ggtgatatca agtagagtt cttccacaaa      780
```

-continued

| | |
|---|---|
| cagaacaaga tgctaaaaaa ggacaaaatg tttcactttt gggtaaatac attcttcata | 840 |
| ccaggaccag aggaaacctc agaaaaagta gaaaatggaa gtctatgtga tcaagaaatc | 900 |
| gatagcattt gcagtataga gcgtgcagat aatgacaagg aatatctagt acttacttta | 960 |
| acaaaaaatg atcttgacaa agcaaataaa gacaaagcca accgatactt ttctccaaat | 1020 |
| tttaaggtga agctgtactt cacaaaaaca gtagaggagc cgtcaaatcc agaggctagc | 1080 |
| agttcaactt ctgtaacacc agatgttagt gacaatgaac ctgatcatta tagatattct | 1140 |
| gacaccactg actctgatcc agagaatgaa ccttttgatg aagatcagca tacacaaatt | 1200 |
| acaaaagtct ga | 1212 |

<210> SEQ ID NO 4
<211> LENGTH: 403
<212> TYPE: PRT
<213> ORGANISM: Artificial Sequence
<220> FEATURE:
<223> OTHER INFORMATION: PTEN

<400> SEQUENCE: 4

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
                20                  25                  30

Ile Ala Met Gly Phe Pro Ala Glu Arg Leu Glu Gly Val Tyr Arg Asn
            35                  40                  45

Asn Ile Asp Asp Val Val Arg Phe Leu Asp Ser Lys His Lys Asn His
        50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

```
Lys Val Glu Asn Gly Ser Leu Cys Asp Gln Glu Ile Asp Ser Ile Cys
        290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Ala Thr Thr Asp
        370                 375                 380

Ser Asp Pro Glu Asn Glu Pro Phe Asp Glu Asp Gln His Thr Gln Ile
385                 390                 395                 400

Thr Lys Val

<210> SEQ ID NO 5
<211> LENGTH: 21
<212> TYPE: DNA
<213> ORGANISM: Artificial Sequence
<220> FEATURE:
<223> OTHER INFORMATION: IGS

<400> SEQUENCE: 5
ttagaaaaaa tacgggtaga a                                         21

<210> SEQ ID NO 6
<211> LENGTH: 6
<212> TYPE: DNA
<213> ORGANISM: Artificial Sequence
<220> FEATURE:
<223> OTHER INFORMATION: Kozak

<400> SEQUENCE: 6 gccacc                                                           6

<210> SEQ ID NO 7
<211> LENGTH: 1470
<212> TYPE: DNA
<213> ORGANISM: Artificial Sequence
<220> FEATURE:
<223> OTHER INFORMATION: NP

<400> SEQUENCE: 7
atgtcttctg tattcgatga gtacgagcag ctcctcgcgg ctcagactcg ccccaatgga    60
gctcatggcg gaggagagaa ggggagcacc ttaaaggtag aagtcccggt attcactctc   120
aacagtgatg acccagaaga tagatggaac tttgcagtgt tttgtcttcg gattgctgtt   180
agcgaggatg ccaacaaacc acttaggcaa ggtgctctca tatctctctt atgttcccac   240
tctcaagtga tgaggaacca tgttgcccct gcggggaaac agaatgaggc cacactggct   300
gttcttgaga tcgatggttt taccaacggc gtgccccagt caacaacag agtggagtg    360 tctgaagaga gagcacagag atttatgatg atagcagggc tctcccctcg gcatgcagc    420 aacggtaccc cgttcgtcac agctggggtt gaagatgatg caccagaaga cattactgat   480
accctggaga ggatcctctc tatccaggct caagtatggg tcacggtggc aaaggccatg   540
actgcatatg agacagcaga tgagtcgaa acaagaagaa tcaataagta catgcagcaa   600
ggcagggtcc agaagaagta catcctccac cccgtatgca ggagcgcaat ccaactcaca   660
```

```
atcagacagt ctctggcggt ccgcatcttt ttggttagcg agcttaagag aggccgcaac      720
acggcaggtg ggacctccac ctattacaac ttggtggggg atgtagactc atacatcagg      780
aacactgggc taactgcatt cttcctgaca cttaaatatg gaattaacac caagacatca      840
gcccttgcac ttagcagcct ctcaggcgat atccagaaaa tgaagcagct catgcgcttg      900
tatcggatga aaggagataa tgcgccgtac atgacattgc tcggtgacag tgaccagatg      960
agctttgcac ctgccgagta tgcacaactt tactcctttg ccatgggtat ggcatcagtc     1020
ctagataaag gaactagcaa ataccaattt gccagggact ttatgagcac atcattctgg     1080
agacttggag tagagtacgc tcaggctcaa ggaagtagca tcaatgagga tatggccgcc     1140
gagctaaagc taaccccagc agcaaggaga ggcctggcag ctgctgccca agagtgtct      1200 gaggagacca gcagcatgga catgcccacc caacaagccg gggtcctcac tggactcagc     1260
gacggaggct cccaagcccc ccaaggtgca ctgaacagat cacaagggca accggacacc     1320
ggggatgggg agacccaatt tctggatctg atgagagcgg tggcaaatag catgagagaa     1380
gcgccaaact ctgcgcaggg caccctcaa ccggggcctc ccccaacccc tgggccctct      1440
caagacaatg acaccgactg ggggtactga                                      1470

<210> SEQ ID NO 8
<211> LENGTH: 1188
<212> TYPE: DNA
<213> ORGANISM: Artificial Sequence
<220> FEATURE:
<223> OTHER INFORMATION: P

<400> SEQUENCE: 8
atggccacct ttacagatgc ggagatcgac gagctatttg agaccagtgg aactgtcatt       60
gacagcataa ttacggccca gggaaaacca gtagagactg ttggaaggag tgcaatccca      120
caaggcaaaa ctaaggcttt gagcgcagca tgggagaagc atgggagcat ccagtcacca      180
gccagccaag acaccctga tcgacaggac agatcagata acaactgtc cacacccgag       240 caagcgagtc caaacgacag ccccccagcc acatccactg accagcctcc cactcaggct      300
gcagatgagg ccggcgatac acagctcaag accggagcaa gcaactctct gctgtcgatg      360
cttgataaac tcagcaataa gtcatctaat gctaaaaagg gcccagggtc gagccctcaa      420
gaaaggcatc atcaacgtct gactcaacaa caggggagtc aacaaagccg cggaaacagc      480
caagagagac cgcagaacca ggccaaggcc atccctggaa accaggtcac agacgcgaac      540
acagcatatc atggacaatg ggaggagtca caactatcag ctggtgcaac ccatcatgct      600
ctccgatcag agcagagcca agacaatact cctgcacctg tggatcatgt ccagctacct      660
gtcgactttg tgcaggcgat gatgtctatg atggaggcga tatcacagag ggtaagtaaa      720
gttgactatc agctggacct tgtcttgaaa cagacatctt ctatccccat gatgcggtct      780
gaaatccagc agctgaaaac gtctgttgcg gtcatggaag ccaatttggg catgatgaag      840
atcctggacc ctggttgtgc caacgtttca tctctaagtg atctacgggc agttgcccga      900
tcccacccgg tttaatttc tggccccgga gacccatctc cttatgtgac ccaagggggc      960
gaaatggcac tcaataaact ttcgcaaccg gtgcaacacc cctctgaatt gattaaaccc     1020
gccacggcaa gcgggcctga tataggagtg agaaagaca ctgtccgtgc attgatcatg     1080
tcacgcccta tgcatccgag ctcttcagct aggctcttga gcaaactgga cgcagccgga     1140
tcgattgagg aaatcagaaa aatcaagcgc cttgcactga atggctaa                 1188
```

<210> SEQ ID NO 9
<211> LENGTH: 1095
<212> TYPE: DNA
<213> ORGANISM: Artificial Sequence
<220> FEATURE:
<223> OTHER INFORMATION: M

<400> SEQUENCE: 9

| | | | | | |
|---|---|---|---|---|---|
| atggactcat | ctaggacaat | cgggctgtac | tttgattcta | cccttccttc | tagcaacctg | 60 |
| ctagcattcc | cgatagtcct | acaagacaca | ggggacggga | agaagcaaat | cgccccgcaa | 120 |
| tacaggatcc | agcgtcttga | ctcgtggaca | gacagcaaag | aagactcggt | attcatcacc | 180 |
| acctatggat | tcatctttca | ggttgggaat | gaagaagcca | ctgtcggcat | gatcaatgat | 240 |
| aatcccaagc | gcgagttact | ttccactgcc | atgctatgcc | tagggagtgt | accaaatgtc | 300 |
| ggagatcttg | ttgagctggc | aagggcctgc | ctcactatgg | tggtaacatg | caagaagagt | 360 |
| gcaactaaca | ccgagagaat | ggtcttctca | gtagtgcagg | cacccaggt | gctgcaaagc | 420 |
| tgtagggttg | tggcaaacaa | atactcgtcg | gtgaatgcag | tcaagcacgt | gaaagcacca | 480 |
| gagaagattc | ctgggagcgg | aaccctagag | tacaaagtga | actttgtctc | tctgaccgtg | 540 |
| gtgccaagaa | aggacgtcta | caagatacca | actgcagcac | ttaaggtctc | tggctcaagt | 600 |
| ctgtacaatc | ttgcgctcaa | tgtcactatt | gatgtggagg | tagacccgaa | gagcccgttg | 660 |
| gtcaaatccc | tttccaagtc | cgacagtggg | tactatgcta | atctcttctt | acatattggg | 720 |
| cttatgtcca | ctgtagataa | gaaggggaag | aaagtgacat | tgacaagct | ggaaaggaag | 780 |
| ataaggagac | ttgatctatc | tgtagggctt | agtgacgtgc | tcggaccttc | cgtgcttgta | 840 |
| aaggcgagag | gtgcacggac | taagctgctg | gcacctttct | tctctagcag | tgggacagcc | 900 |
| tgctatccca | tagcaaatgc | ctctcctcag | gtggccaaga | tactctggag | ccaaaccgcg | 960 |
| tacctgcgga | gtgtaaaagt | cattatccaa | gcgggcaccc | agcgtgctgt | cgcagtgacc | 1020 |
| gccgaccacg | aggttacctc | tactaagctg | gagaaggggc | ataccattgc | caaatacaat | 1080 |
| cccttcaaga | aatag | | | | | 1095 |

<210> SEQ ID NO 10
<211> LENGTH: 1662
<212> TYPE: DNA
<213> ORGANISM: Artificial Sequence
<220> FEATURE:
<223> OTHER INFORMATION: F

<400> SEQUENCE: 10

| | | | | | |
|---|---|---|---|---|---|
| atgggctcca | gatcttctac | caggatccca | gtacctctta | tgctgaccgt | ccgagtcatg | 60 |
| ttggcactga | gttgcgtctg | tccgaccagc | gcccttgatg | caggcctct | tgcagctgca | 120 |
| gggattgtgg | taacaggaga | caaagcagtc | aacatataca | cctcatctca | gacagggtca | 180 |
| atcataatca | agttactccc | aaatatgccc | aaggataaag | aggcgtgtgc | aaaagccccg | 240 |
| ttggaggcat | acaacaggac | attgactact | ttgctcaccc | cccttggtga | ttctatccgt | 300 |
| aggatacaag | agtctgtgac | cacgtccgga | ggagggaaac | agggacgtct | tataggcgcc | 360 |
| attatcggtg | gtgtagctct | cggggttgca | accgctgcac | agataacagc | agcctcggct | 420 |
| ctgatacaag | ccaatcaaaa | tgctgccaac | atactccggc | taaagagag | cattgctgca | 480 |
| accaatgagg | ctgtgcacga | ggtcactaat | ggattatcac | aactagcagt | ggcagttggg | 540 |
| aagatgcagc | aatttgttaa | tgaccagttt | aataaaacag | ctcaggaatt | ggactgtata | 600 |
| aaaattacac | agcaggttgg | tgtagaactc | aacctgtacc | taactgaatt | gactacagta | 660 |

-continued

```
ttcgggccac aaatcacttc ccctgcctta actcagctga ctatccaggc gctttacaat      720
ctagctggtg ggaatatgga ttacttgttg actaagttag gtgtggggaa caaccaactc      780
agctcattaa ttagtagtgg cctgatcacc ggcaacccta ttctgtacga ctcacagact      840
caactcttgg gtatacaggt aaccctaccc tcagtcggga acctaaataa tatgcgtgcc      900
acctacctgg aaaccttgtc tgtaagtaca accaaaggat ttgcctcagc acttgtccca      960
aaagtagtga cacaggtcgg ttccgtgata aagagcttg acacctcgta ctgtatagag      1020
accgatttgg atctatattg tacaagaata gtgacattcc ctatgtctcc tggtatttat      1080
tcctgtttga gtggcaatac atctgcttgc atgtactcaa agactgaagg cgcactcact      1140
acgccgtata tgaccctcaa aggctcagtt attgctaact gtaagatgac aacatgtaga      1200
tgtgcagacc ccccgggtat catatcgcaa aattatggag aagctgtgtc tctaatagat      1260
aggcaatcat gcaatatctt atccttagac gggataactt tgaggctcag tggggaattt      1320
gatgcaactt atcaaaagaa tatctcaata caagattctc aagtaatagt gacaggcaat      1380
cttgatatct cgactgagct tgggaatgtc aacaactcga taagtaatgc tttggataag      1440
ttagaggaaa gcaacagcaa actagataag gtcaatgtca aactgaccag cacatccgct      1500
cttattacct atatcgtttt aactgtcata tctcttgtat gtggtatact tagcctggtt      1560
ctagcatgct acctgatgta caagcaaaag gcgcaacaga agaccttgtt gtggcttggg      1620
aataataccc tagaccagat gagggccact acaaaaatgt ga                         1662
```

<210> SEQ ID NO 11
<211> LENGTH: 1851
<212> TYPE: DNA
<213> ORGANISM: Artificial Sequence
<220> FEATURE:
<223> OTHER INFORMATION: HN

<400> SEQUENCE: 11

```
atggaccgcg cagttagcca agttgcgcta gagaatgatg aaagagaggc aaagaataca       60
tggcgcttgg tattccggat cgcaatccta ctctcaacgg tggtgacctt agccatctct      120
gcagccgccc ttgcatatag catggaggcc agcacaccta cgatcttgt aggcataccg       180 actgcgatct ctagagcaga ggaaaagatt acatctgcac tcggttccaa tcaagatgta      240
gtagatagga tatataagca ggtggccctc gaatctccac tggcattgct aaacaccgaa      300
tctacaatta tgaacgcaat aacgtctctc tcttatcgaa tcaatggggc cgcaaatagc      360
agcggatgtg gagcacccat tcatgatcca gattatattg gaggaatagg taaagaactt      420
attgtagatg atgctagcga cgtcacatca tactatccct ctgcgttcca agaacacctg      480
aactttatcc cggcgcctac tacaggatca ggttgcactc ggataccctc atttgacatg      540
agcgctaccc actactgtta tactcacaat gtgatattat ctggctgcag agatcactcg      600
cactcacatc aatatttagc acttggtgtg cttcggacat ctgcaacagg agggtattc       660 tttccactc tgcgttccat caatctggat gacacccaaa atcggaagtc ttgcagtgtg      720
agtgcaaccc ccttgggttg tgatatgctg tgctctaaag tcacagagac tgaagaagag      780
gattataact cagctatccc cacgtcgatg gtacatggaa ggttagggtt cgacggccaa      840
taccacgaga aggacctaga tgtcacaaca ctattcgagg actgggtggc aaactaccca      900
ggagtagggg gcgggtcttt tattgacaac cgcgtatggt tccagtttta cggagggcta      960
aaacccaatt cgcccagtga caccgcacaa gaagggaaat atgtaatata caagcgatac     1020
```

```
aatgacacat gtccagatga gcaagattat cagattcaaa tggctaagtc ttcatataag      1080
cctgggcggt ttggagggaa acgcgtacag caggccatct tatctatcaa agtgtcaaca      1140
tccttgggcg aggacccggt actgactgta ccgcccaaca cagtaacact catggggggcc    1200 gaaggcagag ttctcacagt agggacatct catttccttt atcagcgagg gtcatcatac      1260
ttctcccctg ccctactata tcctatgata gtcagcaaca aaacagccac tcttcatagt     1320
ccttatacat tcaatgcctt cactcgacca ggtagtgtcc cttgccaggc ttcagcaaga     1380
tgccctaact catgtgttac cggagtctat actgatccat atcccttggt cttctatagg     1440
aaccacacct tgcgaggggt attcgggacg atgcttgatg ataaacaagc aagactcaac     1500
cctgtatctg cagtatttga cagcatatcc cgcagtcgca taacccgggt gagttcaagc     1560
agcaccaagg cagcatacac aacatcaaca tgttttaaag ttgtaaagac caataaaacc    1620
tattgtctca gcattgccga aatatccaat accctcttcg gggaattcag aatcgtccct    1680
ttactagttg agattctcaa ggatgatggg gttagagaag ccaggtctag ccggttgagt    1740
caactgcgag agggttggaa agatgacatt gtatcaccta tcttttgcga cgccaagaat    1800
caaactgaat accggcgcga gctcgagtcc tacgctgcca gttggccata a              1851
```

<210> SEQ ID NO 12
<211> LENGTH: 6615
<212> TYPE: DNA
<213> ORGANISM: Artificial Sequence
<220> FEATURE:
<223> OTHER INFORMATION: L

<400> SEQUENCE: 12

```
atggcgagct ccggtcccga gagggcggag catcagatta tcctaccaga gtcacacctg      60
tcttcaccat tagtcaagca caaactactc tattactgga aattaactgg gctaccactc     120
cctgacgagt gtgacttcga ccacctcatt ctcagccgac aatggaagaa atacttgaa     180 tcggcctccc ctgacactga gagaatgata aaacttggaa gggcagtgca ccagactctc     240
aaccacaatt ccaagataac cggagtactc catcccaggt gtttagaaga attggctagt    300
attgaggttc ctgactcaac caacaagttt cggaagatcg agaagaaaat ccaaattcac     360
aacacaaggt atggagaact gttcacaaga ctgtgcacgc atgtagagaa gaaattgttg    420
ggatcatctt ggtctaataa tgtcccccgg tcagaagagt tcaacagcat ccgtacagat    480
ccggcattct ggtttcactc aaaatggtcc acaactaagt ttgcatggct ccatataaaa    540
cagattcaaa ggcatctgat tgtggcagca agaacaaggt ccgcagccaa caaattggtg    600
acgctgaccc ataaggtagg ccaagtcttt gttactcctg agcttgtcat tgtgacacat    660
acagatgaga caagttcac gtgtcttacc caggaacttg tgttgatgta tgcagatatg    720
atggagggca gagatatggt caacataata tcatccacgg cggcacatct caggagccta    780
tcagagaaaa ttgatgacat tctgcggtta gtagatgccc tggcaaaaga tctgggtaat    840
caagtctacg atgttgtagc actcatggag ggatttgcat acggcgccgt ccagctgctt    900
gagccgtcag gtacattcgc aggggatttc ttcgcattca acctgcagga gctcaaagac    960
actttgatcg gcctccttcc taaggatata gcagaatctg tgactcacgc aatagccact   1020
gtattctctg gcttagaaca aaatcaagcg gctgagatgc tgtgcctgtt gcgtctatgg    1080
ggccacccat tacttgagtc ccgtattgcg gcaaaagcag taaggagcca atgtgcgca    1140 ccaaaaatgg tagactttga tatgatcctc caggtattgt ctttctttaa aggaacaatc    1200
atcaacggat acagaaagaa gaatgcaggt gtttggccac gtgtcaaagt agatacgata     1260
```

```
tacgggaagg tcattgggca gctacacgct gattcagcgg agatttcaca cgatatcatg   1320
ttgagagagt acaagagttt atctgcgctt gaattcgagc catgtataga atacgaccct   1380
atcaccaatc tgagcatgtt tctaaaagac aaggcgatcg cacacccgaa agacaactgg   1440
ctcgccgcgt ttaggcgaaa ccttctctct gaggaccaga agaaacatgt aaaggaggca   1500
acctctacta accgtctctt gatagagttc ttagagtcaa atgattttga tccatataag   1560
gagatggaat atctgacgac ccttgagtac ctaagagatg acaatgtggc agtatcatac   1620
tcgctcaagg agaaggaagt gaaggttaat gggcggattt ttgctaagct aacaaagaaa   1680
ttaaggaact gtcaagtgat ggcggaaggg atcttagctg accagattgc acctttcttt   1740
caagggaatg gggtcattca ggatagcata tctttaacca agagtatgct agcgatgagt   1800
caattgtctt tcaacagcaa taagaaacgt atcactgact gcaaagaaag agtagcctca   1860
aaccgcaatc acgatcaaaa gagcaagaat cgtcggagag ttgccacttt tataacgact   1920
gacctgcaaa agtactgtct taattggaga tatcagacaa tcaaactgtt cgctcatgcc   1980
atcaatcagc tgatgggctt acctcacttc ttcgaatgga ttcatctaag actaatggat   2040
actacgatgt ttgtaggaga ccctttcaat cccccaagtg acccaactga ctgtgatctc   2100
tcaagagtcc caaatgatga catatatatt gtcagtgcta gaggggtat tgagggatta   2160 tgtcagaagc tatggacaat gatctcaatt gctgcaatcc aacttgctgc agcaagatca   2220
cattgtcgcg tcgcctgtat ggtacagggt gacaatcaag taatagctgt aacgagagag   2280
gtaaggtcag atgactcccc ggaaatggtg ttaacacaat tgcatcaagc cagtgataat   2340
ttcttcaagg aattgattca tgttaatcat ttgattggcc ataatttgaa ggatcgtgaa   2400
acaatcagat cagacacatt cttcatatac agcaaacgaa tattcaaaga tggagcaata   2460
ctcagtcaag tcctcaaaaa ttcatctaaa ttagtgctaa tatcaggcga ccttagtgaa   2520
aacaccgtaa tgtcctgtgc caacattgca tctactatag cacggctgtg cgagaacggg   2580
cttccaaagg atttctgtta ttacttaaac tacctgatga gttgcgtgca gacatacttt   2640
gattctgagt tttccatcac taacagctcg cacccccgatt ctaaccagtc gtggattgaa   2700
gacatctctt ttgtgcactc atatgtcctg accctgccc agctaggggg actgagcaac   2760
ctccaatact caaggctcta cacgaggaac atcggtgacc cgggaactac tgcttttgca   2820
gagatcaagc gattagaagc agtggggtta ctaagtccta gtattatgac taacatctta   2880
actaggccgc ctggaaatgg agattgggcc agtctgtgta acgaccctta ctctttcaat   2940
tttgagactg tcgcgagtcc aaatattgtc cttaagaaac atacacaaag agtcctattt   3000
gaaacttgtt caaatcccct tattatctgg ctgtgcatacag aggataatga ggcagaagag   3060
aaggcgttgg ctgaattttt actcaatcaa gaagtaattc atccacgtgt cgcacatgct   3120
atcatggaag caagctctat aggtaggagg aagcagattc aagggcttgt tgacacaaca   3180
aacaccgtaa tcaagattgc attgactagg aggccacttg gcatcaagag gctgatgcgg   3240
atagttaact actcgagcat gcatgcaatg ctgtttagag acgatgtttt ctcatctaac   3300
aggtctaacc acccccttagt ttcctctaat atgtgttctc tgacgctagc agactatgca   3360
cggaatagaa gctggtcacc attgacgggg ggtagaaaga tactgggtgt atctaatcct   3420
gatactatag aacttgtaga gggtgagatc cttagcgtca gcggaggatg cacaagatgt   3480
gacagcggga tgaacaatt cacttggttc catcttccga gcaatataga actgaccgat   3540
gacaccagca agaatcctcc gatgagagtg ccgtacctcg ggtcaaagac tcaagagagg   3600
```

```
agggccgcct cgcttgcgaa aatagctcat atgtcaccac atgtgaaagc tgctctaagg    3660
gcatcatccg tgttgatctg ggcttatgga gacaacgaag taaattggac tgctgctctt    3720
aaaattgcaa gatctcggtg caatataaac tcagagtatc ttcgactatt gtcccccta     3780 cccacagctg ggaatctcca acatagactg gatgacggca taactcagat gacattcacc    3840
cctgcatctc tctacagggt gtcaccttat attcacatat ccaatgattc tcaaaggtta   3900
ttcacggaag aaggagtcaa agagggaaat gtagtttatc agcaaatcat gctcttgggt    3960
ttatctctaa tcgaatcact cttcccgatg acgacaacca ggacatacga tgagatcaca    4020
ttgcacctcc acagtaaatt tagctgctgt atcagggaag caccggttgc agttcctttc    4080
gagttactcg ggatggcacc agaactaagg acagtgacct caaataagtt tatgtatgat    4140
cctagtcctg tatcggaggg tgactttgcg agacttgact tagctatctt taagagttat    4200
gagcttaatc tagaatcata tcccacaata gagctaatga acattctttc aatatccagc    4260
gggaagttaa tcggccagtc tgtggtttct tatgatgaag atacctccat aaagaatgac    4320
gccataatag tgtatgacaa cacccggaat tggatcagcg aagctcagaa ttcagatgtg    4380
gtccgcctat tcgagtatgc agcacttgaa gtgcttctcg actgttctta tcagctctac    4440
tatctgagag taagaggcct agacaatatc gtgttgtata tgagtgactt atataagaat    4500
atgccaggaa ttctactttc caacattgca gctacaatat ctcatcccat cattcattca    4560
agattgcatg cagtaggcct ggtcaatcac gacgggtcac accaacttgc agacacagat    4620
ttcatcgaaa tgtctgcaaa actattagtc tcttgcactc gacgcgtggt ctcaggttta    4680
tatgcaggga ataagtatga tctgctgttc ccgtctgtct tagatgataa cctgagtgag    4740
aagatgcttc agctgatatc tcggttatgc tgcctgtata cggtgctctt tgctacaaca    4800
agagagatcc cgaaaataag aggcttatct gcagaagaga agtgttcagt acttactgag    4860
tacctactgt cagatgctgt gaaaccatta cttagttctg agcaagtgag ctctatcatg    4920
tctcctaaca tagttacgtt cccagctaat ctatattaca tgtctcggaa gagccttaat    4980
ttgattaggg aaagagagga cagggacact atcttggcat tgttgttccc ccaagagcca    5040
ctacttgagt tccccttagt acaagatatt ggcgctcgag tgaaagatcc attcacccga    5100
caacctgcgg cgttttttaca agaattagat ttgagcgctc cagcaaggta tgacgcattt    5160
acacttagtc aggttcattc tgaacacaca tcaccaaatc cggaggacga ctacttagta    5220
cgatacctgt tcagaggaat agggaccgcg tcctcctctt ggtataaggc atctcacctt    5280
ctttctgtac ctgaggtcag atgtgcaagg cacgggaatt ccttatactt ggcagaagga    5340
agcggagcca ttatgagtct tctcgaactg catgtgccgc atgagactat ctattacaat    5400
acgctcttct caaacgagat gaacccccca cagcggcatt tcggaccgac cccaacacag    5460
tttctgaatt cagttgttta taggaatcta caggcggagg taccatgtaa ggatggattt    5520
gtccaggagt tccgtccatt atggagagag aatacagaag aaagcgatct gacctcagat    5580
aaagcagtgg gttacatcac atctgcagtg ccctaccggt ctgtatcatt gctgcactgt    5640
gacattgaga ttcctccagg atccaatcaa agcttactgg atcaactggc taccaatctg    5700
tctctgattg ccatgcattc tgtaagggag ggcggggtcg tgatcatcaa agtgttgtat    5760
gcaatgggat attacttcca tctactcatg aacttgttca ctccgtgttc tacgaaagga    5820
tatattctct ctaatggcta tgcatgtaga ggggatatgg agtgttacct ggtatttgtc    5880
atgggctatc gagtgggcc tacatttgta catgaggtag tgaggatggc aaaaactcta    5940
gtgcagcggc acgtacact tttgtccaaa tcagatgaga tcacactgac taggttattt    6000
```

```
acctcacagc ggcagcgtgt aacagacatc ctatccagtc ctttaccgag actaataaag      6060
ttcttgagaa agaatatcga tactgcgcta attgaagccg ggggacaacc cgtccgtcca      6120
ttctgtgcag agagcttggt gaggacacta gcggacacaa ctcagatgac ccagatcatc      6180
gctagtcaca ttgacacagt cattcgatct gtgatctaca tggaggctga gggtgatctc      6240
gccgacacag tgttcttatt taccccctac aatctctcta cagacggtaa aaagagaaca      6300
tcacttaaac agtgcacaag gcagatctta gaggtcacaa tattgggtct tagagttgaa      6360
aatctcaata agtaggtga tgtagtcagt ctagtactta aaggtatgat ttctctggag       6420
gacctgatcc ctctaagaac atacttgaag cgtagtacct gccctaagta tttgaagtct      6480
gttctaggta ttactaaact caaagaaatg tttacagaca cctctttatt atacttgact      6540
cgtgctcaac aaaaattcta catgaaaact ataggcaacg cagtcaaggg atactacagt      6600
aactgtgact cttaa                                                      6615
```

```
<210> SEQ ID NO 13
<211> LENGTH: 30
<212> TYPE: DNA
<213> ORGANISM: Artificial Sequence
<220> FEATURE:
<223> OTHER INFORMATION: L2 primer_F

<400> SEQUENCE: 13
acgcgtggtc tcaggtttat atgcagggaa                                       30

<210> SEQ ID NO 14
<211> LENGTH: 31
<212> TYPE: DNA
<213> ORGANISM: Artificial Sequence
<220> FEATURE:
<223> OTHER INFORMATION: L2 primer_R

<400> SEQUENCE: 14
ttaattaaac caaacaaaga tttggtgaat g                                     31

<210> SEQ ID NO 15
<211> LENGTH: 30
<212> TYPE: DNA
<213> ORGANISM: Artificial Sequence
<220> FEATURE:
<223> OTHER INFORMATION: L1 primer_F

<400> SEQUENCE: 15
actagttgag attctcaagg atgatggggt                                       30

<210> SEQ ID NO 16
<211> LENGTH: 30
<212> TYPE: DNA
<213> ORGANISM: Artificial Sequence
<220> FEATURE:
<223> OTHER INFORMATION: L1 primer_R

<400> SEQUENCE: 16
acgcgtcgag tgcaagagac taatagtttt                                       30

<210> SEQ ID NO 17
<211> LENGTH: 29
<212> TYPE: DNA
<213> ORGANISM: Artificial Sequence
<220> FEATURE:
<223> OTHER INFORMATION: F-HN primer_F
```

<400> SEQUENCE: 17
ggcgccatta tcggtggtgt agctctcgg                                29

<210> SEQ ID NO 18
<211> LENGTH: 30
<212> TYPE: DNA
<213> ORGANISM: Artificial Sequence
<220> FEATURE:
<223> OTHER INFORMATION: F-HN primer_R

<400> SEQUENCE: 18
actagtaaag ggacgattct gaattccccg                               30

<210> SEQ ID NO 19
<211> LENGTH: 30
<212> TYPE: DNA
<213> ORGANISM: Artificial Sequence
<220> FEATURE:
<223> OTHER INFORMATION: P-M-F primer_F

<400> SEQUENCE: 19
ccgcggaaac agccaagaga gaccgcagaa                               30

<210> SEQ ID NO 20
<211> LENGTH: 33
<212> TYPE: DNA
<213> ORGANISM: Artificial Sequence
<220> FEATURE:
<223> OTHER INFORMATION: P-M-F primer_R

<400> SEQUENCE: 20
ggcgccaacc gggatccaga atcttctacc cgt                           33

<210> SEQ ID NO 21
<211> LENGTH: 30
<212> TYPE: DNA
<213> ORGANISM: Artificial Sequence
<220> FEATURE:
<223> OTHER INFORMATION: NP-P primer_F

<400> SEQUENCE: 21
gtttaaacac caaacagaga atccgtaagg                               30

<210> SEQ ID NO 22
<211> LENGTH: 30
<212> TYPE: DNA
<213> ORGANISM: Artificial Sequence
<220> FEATURE:
<223> OTHER INFORMATION: NP-P primer_R

<400> SEQUENCE: 22
ccgcggcttt gttgactccc ctgttgttga                               30

<210> SEQ ID NO 23
<211> LENGTH: 20
<212> TYPE: DNA
<213> ORGANISM: Artificial Sequence
<220> FEATURE:
<223> OTHER INFORMATION: pBR322-NP primer_F

<400> SEQUENCE: 23
ttctcgcttc cggcggcatc                                          20

<210> SEQ ID NO 24
<211> LENGTH: 47

<212> TYPE: DNA
<213> ORGANISM: Artificial Sequence
<220> FEATURE:
<223> OTHER INFORMATION: pBR322-NP primer_R

<400> SEQUENCE: 24
ccgcttctac ccgtattttt tctaagcaga ggaattggga tgacctc        47

<210> SEQ ID NO 25
<211> LENGTH: 48
<212> TYPE: DNA
<213> ORGANISM: Artificial Sequence
<220> FEATURE:
<223> OTHER INFORMATION: P-M primer_F

<400> SEQUENCE: 25
tacgggtaga agcggccgcg gccggcccca caccccaccc ctcaatcc       48

<210> SEQ ID NO 26
<211> LENGTH: 23
<212> TYPE: DNA
<213> ORGANISM: Artificial Sequence
<220> FEATURE:
<223> OTHER INFORMATION: P-M primer_R

<400> SEQUENCE: 26
ccgggatcca gaatcttcta ccc                                  23

<210> SEQ ID NO 27
<211> LENGTH: 21
<212> TYPE: DNA
<213> ORGANISM: Artificial Sequence
<220> FEATURE:
<223> OTHER INFORMATION: F-HN primer_F

<400> SEQUENCE: 27
gattctggat cccggttggc g                                    21

<210> SEQ ID NO 28
<211> LENGTH: 21
<212> TYPE: DNA
<213> ORGANISM: Artificial Sequence
<220> FEATURE:
<223> OTHER INFORMATION: F-HN primer_R

<400> SEQUENCE: 28
ccgccatcac ttgacagttc c                                    21

<210> SEQ ID NO 29
<211> LENGTH: 20
<212> TYPE: DNA
<213> ORGANISM: Artificial Sequence
<220> FEATURE:
<223> OTHER INFORMATION: L primer_F

<400> SEQUENCE: 29
gtcaagtgat ggcggaaggg                                      20

<210> SEQ ID NO 30
<211> LENGTH: 20
<212> TYPE: DNA
<213> ORGANISM: Artificial Sequence
<220> FEATURE:
<223> OTHER INFORMATION: L primer_R

<400> SEQUENCE: 30
cgccggaagc gagaagaatc                                            20

<210> SEQ ID NO 31
<211> LENGTH: 20
<212> TYPE: DNA
<213> ORGANISM: Artificial Sequence
<220> FEATURE:
<223> OTHER INFORMATION: pBR322-NP-P primer_F

<400> SEQUENCE: 31
ttctcgcttc cggcggcatc                                            20

<210> SEQ ID NO 32
<211> LENGTH: 35
<212> TYPE: DNA
<213> ORGANISM: Artificial Sequence
<220> FEATURE:
<223> OTHER INFORMATION: pBR322-NP-P primer_R

<400> SEQUENCE: 32
ttctacccgt attttttctt aagtttgcag agagg                            35

<210> SEQ ID NO 33
<211> LENGTH: 43
<212> TYPE: DNA
<213> ORGANISM: Artificial Sequence
<220> FEATURE:
<223> OTHER INFORMATION: M-F primer_F

<400> SEQUENCE: 33
aaaatacggg tagaagcggc cgcccaaggt ccaacacccc gag                   43

<210> SEQ ID NO 34
<211> LENGTH: 21
<212> TYPE: DNA
<213> ORGANISM: Artificial Sequence
<220> FEATURE:
<223> OTHER INFORMATION: M-F primer_R

<400> SEQUENCE: 34
gacgtcgcta gcatcatcta c                                          21

<210> SEQ ID NO 35
<211> LENGTH: 20
<212> TYPE: DNA
<213> ORGANISM: Artificial Sequence
<220> FEATURE:
<223> OTHER INFORMATION: HN-L primer_F

<400> SEQUENCE: 35
gatgctagcg acgtcacatc                                            20

<210> SEQ ID NO 36
<211> LENGTH: 21
<212> TYPE: DNA
<213> ORGANISM: Artificial Sequence
<220> FEATURE:
<223> OTHER INFORMATION: HN-L primer_R

<400> SEQUENCE: 36
ccgccatcac ttgacagttc c                                          21

<210> SEQ ID NO 37
<211> LENGTH: 20
<212> TYPE: DNA
<213> ORGANISM: Artificial Sequence

```
<220> FEATURE:
<223> OTHER INFORMATION: L primer_F

<400> SEQUENCE: 37
gtcaagtgat ggcggaaggg                                              20

<210> SEQ ID NO 38
<211> LENGTH: 20
<212> TYPE: DNA
<213> ORGANISM: Artificial Sequence
<220> FEATURE:
<223> OTHER INFORMATION: NDV check primer_F

<400> SEQUENCE: 38
cgccggaagc gagaagaatc                                              20

<210> SEQ ID NO 39
<211> LENGTH: 23
<212> TYPE: DNA
<213> ORGANISM: Artificial Sequence
<220> FEATURE:
<223> OTHER INFORMATION: NDV check primer_F

<400> SEQUENCE: 39
ccacaattcc aagataaccg gag                                          23

<210> SEQ ID NO 40
<211> LENGTH: 23
<212> TYPE: DNA
<213> ORGANISM: Artificial Sequence
<220> FEATURE:
<223> OTHER INFORMATION: NDV check primer_R

<400> SEQUENCE: 40
gctgccacaa tcagatgcct ttg                                          23

<210> SEQ ID NO 41
<211> LENGTH: 21
<212> TYPE: DNA
<213> ORGANISM: Artificial Sequence
<220> FEATURE:
<223> OTHER INFORMATION: NP-PTEN-P check primer_F

<400> SEQUENCE: 41
aacagatcac aagggcaacc g                                            21

<210> SEQ ID NO 42
<211> LENGTH: 22
<212> TYPE: DNA
<213> ORGANISM: Artificial Sequence
<220> FEATURE:
<223> OTHER INFORMATION: NP-PTEN-P check primer_R

<400> SEQUENCE: 42
tggttttccc tgggccgtaa tt                                           22

<210> SEQ ID NO 43
<211> LENGTH: 21
<212> TYPE: DNA
<213> ORGANISM: Artificial Sequence
<220> FEATURE:
<223> OTHER INFORMATION: P-PTEN-M check primer_F

<400> SEQUENCE: 43
ggcaagcggg cctgatatag g                                            21
```

<210> SEQ ID NO 44
<211> LENGTH: 21
<212> TYPE: DNA
<213> ORGANISM: Artificial Sequence
<220> FEATURE:
<223> OTHER INFORMATION: P-PTEN-M check primer_R

<400> SEQUENCE: 44
cttcccgtcc cctgtgtctt g                                    21

<210> SEQ ID NO 45
<211> LENGTH: 25
<212> TYPE: DNA
<213> ORGANISM: Artificial Sequence
<220> FEATURE:
<223> OTHER INFORMATION: Vaccinia virus check primer_F

<400> SEQUENCE: 45
atgacgatga aaatgatggt acata                                25

<210> SEQ ID NO 46
<211> LENGTH: 25
<212> TYPE: DNA
<213> ORGANISM: Artificial Sequence
<220> FEATURE:
<223> OTHER INFORMATION: Vaccinia virus check primer_R

<400> SEQUENCE: 46
ctccaatact actgtagttg taagg                                25

<210> SEQ ID NO 47
<211> LENGTH: 25
<212> TYPE: DNA
<213> ORGANISM: Artificial Sequence
<220> FEATURE:
<223> OTHER INFORMATION: Kozak PTEN primer_F

<400> SEQUENCE: 47
gccaccatga cagccatcat caaag                                25

<210> SEQ ID NO 48
<211> LENGTH: 25
<212> TYPE: DNA
<213> ORGANISM: Artificial Sequence
<220> FEATURE:
<223> OTHER INFORMATION: Kozak PTEN primer_R

<400> SEQUENCE: 48
cgctcagact tttgtaattt gtgta                                25

<210> SEQ ID NO 49
<211> LENGTH: 33
<212> TYPE: DNA
<213> ORGANISM: Artificial Sequence
<220> FEATURE:
<223> OTHER INFORMATION: Not I Kozak primer_F

<400> SEQUENCE: 49
atacgggtag aagcggccgc caccatgaca gcc                       33

<210> SEQ ID NO 50
<211> LENGTH: 36
<212> TYPE: DNA
<213> ORGANISM: Artificial Sequence
<220> FEATURE:
<223> OTHER INFORMATION: Not I Kozak primer_R

```
<400> SEQUENCE: 50
tggaccttgg gcggccgctc agactttttgt aatttg                              36

<210> SEQ ID NO 51
<211> LENGTH: 21
<212> TYPE: DNA
<213> ORGANISM: Artificial Sequence
<220> FEATURE:
<223> OTHER INFORMATION: PTEN Real-time primer_F

<400> SEQUENCE: 51
tcccagtcag aggcgctatg t                                               21

<210> SEQ ID NO 52
<211> LENGTH: 20
<212> TYPE: DNA
<213> ORGANISM: Artificial Sequence
<220> FEATURE:
<223> OTHER INFORMATION: PTEN Real-time primer_R

<400> SEQUENCE: 52
ggcagaccac aaactgagga                                                 20

<210> SEQ ID NO 53
<211> LENGTH: 21
<212> TYPE: DNA
<213> ORGANISM: Artificial Sequence
<220> FEATURE:
<223> OTHER INFORMATION: PTEN Real-time probe

<400> SEQUENCE: 53
tgcaagttcc gccactgaac a                                               21
```

ONCOLYTIC VIRUS FOR TREATING BRAIN TUMORS USING RECOMBINANT NEWCASTLE DISEASE VIRUS INTO WHICH NEWCASTLE DISEASE VIRUS VECTOR-BASED PTEN GENE IS INSERTED AND COMPOSITION FOR TREATING BRAIN TUMORS USING SAME

CROSS REFERENCE TO RELATED APPLICATIONS

This application is a National Stage of International Application No. PCT/KR2021/006924, filed Jun. 3, 2021, claiming priority to Korean Patent Application No. 10-2021-0038880, filed Mar. 25, 2021, the entire disclosures of which are incorporated herein by reference.

TECHNICAL FIELD

The present invention relates to a development of an oncolytic virus for treating brain tumors and a composition for treatment and a therapeutic agent using the same, and more particularly, to an oncolytic virus for treating brain tumors using a recombinant Newcastle disease virus into which a Newcastle disease virus vector (NDV)-based PTEN (phosphatase and tensin homolog) gene is inserted and a composition for treating brain tumors using the same.

BACKGROUND ART

Glioblastoma or brain tumor is the most common and serious symptom of cancer derived and generated from glial cells (glia, neuroglia) in the brain. It is also a serious cancer that occurs in the central nervous system. The general treatment used for such glioblastoma or brain tumor is a combination of surgery and methods such as chemotherapy or radiation therapy. The most common clinical symptoms that occur in patients are persistent headache, vomiting, aniseikonia, loss of taste, sudden personality change, dizziness, brain hemorrhage, etc. Various symptoms may occur depending on the area of the brain tissue affected by the cancerous tissue. It is known that more than 75% of malignant brain neoplasms are brain tumors or glioblastomas. The stage of malignant brain tumor and the shape of the brain tumor are derived from glial cells and are affected by how and in what form they are formed in the brain tissue. For these reasons, an effective therapeutic agent for each patient has not yet been developed.

Oncolytic virus treatment is taking a new approach as a new biopharmaceutical for cancer treatment and has made significant progress at experimental and clinical levels. Recently, the oncolytic virus used for virus treatment uses a method that uses the virus itself having oncolytic properties, a method that uses a virus that specifically acts on cancer cells and inserts a gene that has an effect on killing cancer cells, or both methods.

Accordingly, studies on various cancer treatment effects using Newcastle Disease Virus (NDV) are in progress. NDV is known to have an oncolytic effect that induces cancer cell death by actively proliferating only in cancer cells by itself. It is known that interferon-α induced in normal cells has an oncolytic effect due to the very weak or non-responsive properties in cancer cells. According to recent studies, it has been found to have a cancer cell killing effect by inducing an immune response to cancer cells by a specific viral protein and enhancing the apoptosis effect. When NDV infects normal cells, it has been found that the RNA genome of the NDV is easily destroyed by an immune response by interferon-α of the infected cells and thus does not proliferate, so it is not infective to mammals and does not form antibodies by the virus. These characteristics of NDV can be an advantage as a cancer therapeutic agent using a virus. In the 1950s, the cancer cell killing effect was tested using a velogenic NDV strain, and in certain cases, a clinical trial was also conducted for cancer patients. Various studies and clinical trials have provided a lot of evidence that cancer treatment using NDV has good prospects, and NDV does not infect normal mammalian cells, and maintains an effect on killing cancer cells or inhibiting growth of cancerous tissue without the side effects of repeated NDV inoculation. Also in clinical trials, there were cases where cancer patients survived for more than 5 years after being vaccinated with NDV for 5 years. However, a velogenic NDV is a deadly virus that infects chickens and is very dangerous for the poultry industry. Hence, there was a limit to the development of a cancer therapeutic agent with a velogenic virus.

In the 2000s, many scientists started developing an oncolytic virus using a mesogenic NDV. However, as the pathogenicity of the mesogenic NDV was reduced, it was identified that the efficacy was lower than that of the velogenic NDV in terms of cancer cell killing effect or cancer tissue growth inhibitory effect. The main reason for the low efficacy is that the mesogenic NDV has the same nature as a lysogenic virus and has a disadvantage that re-infection does not easily occur from an infected cancer cell to another cancer cell. Nevertheless, the biggest advantage of continuing to use NDV for treating brain tumors is that NDV can pass through the blood-brain barrier (BBB) through the nervous system infection, spread to and infect the brain, thereby infecting brain tumor cells, and killing brain tumor cells. In order to overcome these shortcomings of mesogenic NDV, a recombinant NDV containing various cancer cell death and cancer tissue growth inhibitory genes has been developed. The recombinant NDV into which the tumor inhibitory gene is inserted shows better efficacy than the existing mesogenic NDV and continues to develop through various studies related to NDV.

PTEN (phosphatase and tensin homolog) is a well-known tumor inhibitory gene and is an enzyme that removes 3' phosphate of PIP3 (Phospho-inositol triphosphate) and converts the same into PIP2 (phospho-inositol biphosphate). It regulates cell migration and viable cell proliferation through dephosphorylation. In addition, it is known that the enzyme activity of PTEN is lost due to deletion or mutation of the PTEN gene, thereby inhibiting apoptosis and actively promoting cell proliferation during cancer progression. Abnormalities in the PTEN gene are known to cause cancer, including prostate cancer, endoderm-derived cancer, breast cancer, lung cancer, etc. Recently, abnormalities in the phosphatidylinositol 3-OH kinase pathway due to PTEN abnormalities in more than 50% of brain tumor patients have been found to be an important cause. The attenuated phosphatase activity of PTEN is closely related to cancer suppression and is an important gene for cell cycle regulation and proliferation regulation. Accordingly, the present invention is to provide a method for developing a viral therapeutic agent for brain tumors by inserting the PTEN gene, which is known to cause brain tumors, into a recombinant NDV, and more specifically, to an oncolytic virus for treating brain tumors using a recombinant Newcastle disease virus into which a Newcastle disease virus vector (NDV)-based PTEN gene is inserted and a composition for treating brain tumors using the same.

DISCLOSURE

Technical Problem

An aspect of the present invention is to provide an LVP-K1 vector for inserting a foreign gene containing Newcastle Disease Virus (NDV) cDNA and a transgene cassette.

In addition, another aspect of the present invention is to provide a recombinant Newcastle disease virus containing the LVP-K1 vector for inserting the foreign gene and a tumor inhibitory gene PTEN (phosphatase and tensin homolog) gene.

In addition, another aspect of the present invention is to provide a pharmaceutical composition for prevention or treatment of brain tumors containing the recombinant Newcastle disease virus or a virus purified therefrom.

In addition, another aspect of the present invention is to provide a method for preventing or treating brain tumors including administering the recombinant Newcastle disease virus or a virus purified therefrom.

In addition, another aspect of the present invention is to provide a method for providing information on brain tumor prevention or treatment including administering a recombinant Newcastle disease virus or a virus purified therefrom.

In addition, another aspect of the present invention is to provide a method for producing a recombinant Newcastle disease virus containing the PTEN gene and capable of being expressed as a protein in cancer cells.

Finally, another aspect of the present invention is to provide a method for evaluating an effect of treating brain tumors in animals.

Technical Solution

One aspect of the present invention provides an LVP-K1 vector for inserting a foreign gene containing a Newcastle Disease Virus (NDV) cDNA and a transgene cassette containing genes encoding NP, P, M, F, HN and L proteins as active ingredients, in which the transgene cassette consists of an IGS sequence (GE (gene end), IG (intergenic sequence) and GS (gene start)) and an MCS (multiple cloning site).

In one embodiment of the present invention, the "vector" may be represented by a nucleotide sequence represented by SEQ ID NO: 1 but is not limited thereto.

In one embodiment of the present invention, the "transgene cassette" may be inserted between an NP gene and a P gene of a Newcastle disease virus but is not limited thereto.

In one embodiment of the present invention, the "LVP-K1 vector" may further include a kozak sequence represented by a nucleotide sequence represented by SEQ ID NO: 6 but is not limited thereto.

In addition, the present invention provides an LVP-K1-PTEN vector further including a PTEN gene represented by a nucleotide sequence represented by SEQ ID NO: 3 in the LVP-K1 vector.

In one embodiment of the present invention, the "vector" may be represented by a nucleotide sequence represented by SEQ ID NO: 2 but is not limited thereto.

In one embodiment of the present invention, the "PTEN gene" may be introduced between the NP and P genes but is not limited thereto.

In addition, the present invention provides a recombinant Newcastle disease virus (Accession No.: KCTC 14422BP) into which the LVP-K1-PTEN vector is introduced (Depository Institution: Korean Collection for Type Cultures (KCTC) of Korea Research Institute of Biotechnology and Bioscience; Accession No.: KCTC 14496BP; Deposit Date: 20210312).

In addition, the present invention provides a pharmaceutical composition for preventing or treating brain tumors containing a recombinant Newcastle disease virus (Accession No.: KCTC 14422BP) as an active ingredient.

In one embodiment of the present invention, the composition may further include an antigen purified from a recombinant Newcastle disease virus but is not limited thereto.

In addition, the present invention provides a method for preventing or treating brain tumors, in which the method includes administering the composition to an animal.

In addition, the present invention provides a method for providing information on brain tumor prevention or treatment, in which the method includes administering the composition to an animal.

In addition, the present invention provides a method for evaluating an effect of preventing or treating brain tumors in an animal, in which the method includes administering the composition to an animal.

In one embodiment of the present invention, the "method" may be measuring and evaluating changes in cancer cells or cancer tissues of animals but is not limited thereto.

Finally, the present invention provides a method for producing a recombinant Newcastle disease virus, in which the method includes: inoculating the recombinant Newcastle disease virus into a host cell line; culturing the host cell line; and obtaining the recombinant Newcastle disease virus from a culture of the host cell line.

Advantageous Effects

It has been identified that it is possible to treat brain tumors through brain tumor apoptosis by expressing PTEN protein in cancer cells when a PTEN gene is included in a Newcastle disease virus (NDV) that can spread to the human brain for the purpose of treating brain tumors caused by abnormalities in the PTEN (phosphatase and tensin homolog) gene, which is identified to be more than 50% of the causes of brain tumors of the present invention. Accordingly, for the brain tumor treatment effect, the present invention developed LVP-K1-PTEN oncolytic virus to complete the development of a safe and effective brain tumor treatment, which may contribute to treatment of patients with brain tumors and brain tumor treatment by inhibiting the deterioration of brain tumors.

DESCRIPTION OF DRAWINGS

FIG. 1A shows a process of synthesizing an NDV VG/GA strain of the present invention with cDNA and inserting the same into a pBR322 vector, and FIG. 1B is a diagram showing a gene schematic diagram of LVP-K1-PTEN and LVP-K2-PTEN vectors.

FIG. 2 is a diagram showing RT-PCR products for identifying a virus, a PTEN gene, and removal of vaccinia virus after LVP-K1-PTEN and LVP-K2-PTEN virus construction of the present invention.

FIG. 3 is a diagram showing a relative amount of PTEN mRNA transcription in LVP-K1-PTEN and LVP-K1 virus-infected T98G cells of the present invention (* indicates P value 0.05 or less, and ** indicates P value 0.01 or less).

FIG. 4 is a diagram showing a relative expression level of PTEN proteins in T98G cells infected with LVP-K1-PTEN, LVP-K2-PTEN, and LVP-K1 viruses of the present invention using Western blot.

FIG. 5 is a diagram showing the apoptosis of T98G cells infected with LVP-K1-PTEN and LVP-K1 viruses of the present invention (* indicates P value 0.05 or less, and ** indicates P value 0.01 or less).

BEST MODES OF THE INVENTION

Figure 1B:
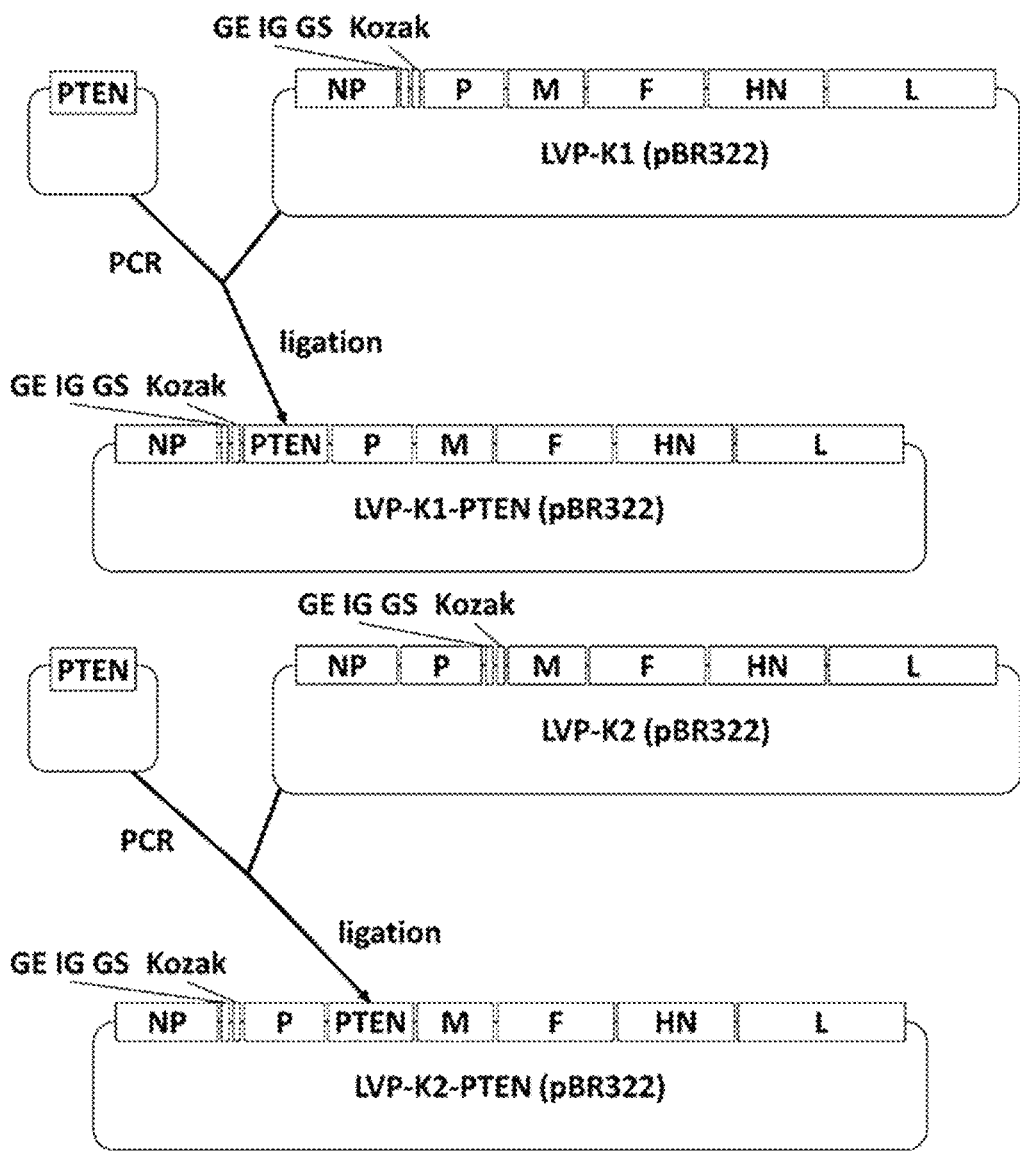

Hereinafter, the present invention will be described in detail by way of embodiments of the present invention with reference to the accompanying drawings. However, the following examples are provided by way of illustration of the present invention. When it is determined that the specific description of known techniques or configuration well known to those skilled in the art unnecessarily obscure the gist of the present invention, the detailed description therefor may be omitted, and the present invention is not limited thereto. The present invention allows various modifications and applications within the description of the claims to be described later and the scope of equivalents interpreted therefrom.

Further, terminologies used herein are terms used to properly represent preferred embodiments of the present invention. It may vary depending on the intent of users or operators, or custom in the art to which the present invention belongs. Accordingly, the definitions of these terms should be based on the contents throughout this specification. In the entire specification, when a part is referred to as "comprising" a component, it means that it may further include other components without excluding other components unless specifically described otherwise.

Throughout the specification, "%" used to refer to the concentration of specific substance is (weight/weight) % for solid/solid, (weight/volume) % for solid/liquid and (volume/volume) % for liquid/liquid, unless specified otherwise.

Hereinafter, the present invention will be described in more detail.

The present invention provides an LVP-K1 vector for inserting a foreign gene containing a Newcastle Disease Virus (NDV) cDNA and a transgene cassette containing genes encoding NP, P, M, F, HN and L proteins as active ingredients.

In addition, the transgene cassette consists of an IGS sequence (gene end (GE), intergenic sequence (IG), and gene start (GS)) and a multiple cloning site (MCS).

As used herein, the term "Newcastle disease virus (NDV)" belongs to a paramyxovirus having a (−) sense RNA genome of about 15 kb and is known as a safe virus for mammals without human infectivity. NDV genomic RNA has an extragenic leader sequence of about 30 bases and a tail sequence of about 50 bases. Two sequences at both termini are known to control the transcription and replication of viral genes and the encapsidation of newly synthesized RNA genomes into viral particles. The NDV gene configuration consists of six genes including NP, P, M, F, HN and L between both terminal leader and tail genes, and each gene encodes a nucleoprotein (NP), a phosphoprotein (P), a matrix protein (M), a fusion protein (F), a hemagglutinin-neuraminidase protein (HN), and a large protein (L).

In the Newcastle disease virus, an IGS (GE-IG-GS) sequence exists between each gene, and each gene undergoes a transcriptional process in the initial stage of host cell infection to synthesize a movement protein to the endoplasmic reticulum (ER) of the host cell. Then, when the amount of M protein synthesis rises above a certain level, a (+) sense RNA genome is synthesized, and a (−) sense RNA genome is synthesized using this as a template. The finished virus particles are expelled out of the cell.

It is known that the "ability of the Newcastle disease virus to introduce foreign genes" is up to 6 kb, and the introduction of foreign genes has been mainly made between the P and M genes and between the HN and L genes. However, although it is known that all of the foreign genes may be introduced between the six genes, it is known that each location has an effect on mRNA expression, protein expression, and, in severe cases, virus proliferation. However, quantitative comparison tests for each location have not been performed. There is a GE-IG-GS gene between each gene. In particular, in the case of an IG gene, it is made up of 1 or 2 nucleotides between NP-P, P-M and M-F, 35 nucleotides between F-HN, and 47 nucleotides between HN-L. After virus infection, the (−) sense RNA genome synthesizes the mRNA of each protein at the initial stage of infection by the NP, P, and L proteins possessed by NDV, and the synthesized mRNA moves to the endoplasmic reticulum of the host cell to synthesize the protein of each gene. Thereafter, the (+) sense RNA genome is synthesized by the interaction of the NP, P, and L proteins with the M protein, and many copies of the (−) sense RNA genome are synthesized using this as a template and released out of the host cell. It is known that the amount of mRNA synthesis for autologous protein production at the time of initial infection is the most at the N-terminus, in other words, NP mRNA is synthesized the most, and the mRNA synthesis decreases as it moves away from the N-terminus afterward.

For cDNA construction of a Newcastle disease virus, a method of making the NDV (−) sense RNA genome into multiple fragments of double-stranded DNA through the reverse transcription polymerase chain reaction (RT-PCR) method, and then re-ligating each fragment to create a cDNA clone of the entire NDV is being used. In cDNA preparation using this method, point mutation is highly likely to occur due to the nature of reverse transcriptase, so after the cDNA is finished preparing, the gene sequence of 15 kb is identified through sequencing. When one or more point mutation occurs, a process of making cDNA from the NDV genome needs to be repeated again. Recombinant NDV is constructed by inserting the cDNA fragment into the pBR322 vector.

In addition, a transgene cassette was created and inserted so that a foreign gene may be easily introduced into a position into which the foreign gene may be inserted so that the antigen protein may be expressed or operated through a recombinant Newcastle disease virus. The transgene cassette is composed of a GE-IG-GS sequence and a multiple cloning site (MCS) in front of the N-terminus of the foreign gene insertion site and may be constructed by inserting the transgene cassette between the NP and P genes, between the P and M genes, and between the HN and L genes in compliance with the rule of six together with various restriction enzyme sequences. Preferably, the transgene cassette may be inserted between the NP and P genes, and between the P and M genes, and more preferably, the transgene cassette may be inserted between the NP and P genes.

According to one embodiment of the present invention, the LVP-K1 vector for inserting the foreign gene may construct a recombinant NDV virus through an overlap cloning method after putting the transgene cassette in a perfectly made recombinant NDV between each gene, dividing it into 4 fragments of DNA, ligating each NDV fragmented gene to pBR322 plasmid DNA, and then performing transformation into TOP10 *E. coli* to construct and store 4 types of recombinant strains, and then separating the gene from each recombinant *E. coli* strain when introducing a new gene, and obtaining a fragment of the gene using PCR, but is not limited thereto.

In addition, the vector constructed by the above method prevents point mutation that occurs during the process of making a recombinant Newcastle disease virus each time and has a feature that a foreign gene may be easily inserted into the NDV cDNA through a multiple cloning site (MCS).

In addition, the LVP-K1 vector for inserting the foreign gene may be composed of the nucleotide sequence represented by SEQ ID NO: 1 and includes a functionally equivalent substance thereto. The term "functionally equivalent substance" refers to a gene or gene combination including a sequence having at least 70%, preferably at least 80%, and more preferably at least 90% of homology with a gene sequence represented by SEQ ID NO: 1 as a result of a substitution or deletion of a nucleotide and exhibiting substantially identical physiological activity to the gene having the gene sequence represented by SEQ ID NO: 1.

Next, the present invention provides a recombinant Newcastle disease virus including the LVP-K1 vector for inserting the foreign gene and a gene encoding a human PTEN (phosphatase and tensin homolog) protein.

In addition, the "PTEN gene" is known to produce energy by converting glucose into lactic acid while rapidly growing cancer cells in brain cells. In this series of metabolic processes, the PTEN-PI3K-AKT-mTOR signaling system plays a central role in glucose metabolism and is related to increased ATP consumption due to glycosylation in glucose uptake and transport lipogenesis-inducing protein synthesis. A series of metabolic processes caused by abnormalities in the PTEN gene are being studied to be closely related to cancer cell growth. It is a gene established based on the PTEN gene information (Gene ID: NCBI Reference Sequence: NG_007466.2).

In addition, the "PTEN protein" refers to a protein expressed in cells of various human organs, and preferably may be a PTEN protein expressed in glial cells, and the exact amino acid sequence may be the sequence listed by SEQ ID NO: 4.

As for a method for securing the PTEN protein-coding gene, a polymerase chain reaction (PCR) method using either artificially synthesized using a gene synthesizer or a primer capable of complementary binding from the PTEN gene present in human cells may be used. Depending on the expression system, there may be differences from the gene encoding the human PTEN protein due to codon optimization. Therefore, the gene encoding the recombinant PTEN may exist in the form of various nucleotide sequences including amino acid residues of the PTEN protein.

The "host cell into which the PTEN protein gene is introduced" may be a prokaryotic or eukaryotic cell, and any cell having a high expression rate of the introduced PTEN protein may be used without limitation. Examples include *E. coli*, mammalian cell lines, insect cell lines, fungi, yeast, eukaryotic and prokaryotic host cells such as recombinant viruses, and the like.

In addition, "expression of PTEN protein" may be expressed as a simple subunit protein or may exist in a form that is exposed to the outside by binding to a specific virus or virus surface. Preferably, the gene is transferred to a host cell by a virus and expressed in a cell line. Preferably, the normal intracellular expression and functional activity of the PTEN protein transferred by the virus will be expressed to be maintained.

Examples of viruses that may be used for the expression of the PTEN protein include a lentivirus, a retrovirus, a vaccinia virus, an adenovirus, and an adeno-associated virus, a cytomegalovirus, a Sendai virus, a poxvirus, a Newcastle disease virus, and an alphavirus. Any virus capable of expressing a protein through introduction of a foreign gene and capable of producing high stability, high expression ability and high viral titer may be used without limitation. Preferably, it may include a poxvirus, a flavivirus, an alphavirus, and a Newcastle disease virus as an enveloped virus. More preferably, it may be a Newcastle disease virus (NDV) that is a safe virus without human infectivity and capable of producing a high viral titer.

The "Newcastle disease virus" is a legal infectious disease that infects chickens and causes neurological and respiratory symptoms and is a very lethal virus for chickens. According to the pathogenicity, it is divided into velogenic, mesogenic, and lentogenic Newcastle disease viruses, all of which may be used in the production of PTEN gene transfer virus vector vaccines, but preferably mesogenic and lentogenic viruses may be used. More preferably, it may be a recombinant virus using a lentogenic virus strain.

The transgene cassette expressing the PTEN gene, MCS, and NP and P genes of the NDV strains are genes or a combination of genes designed to exert the effect of inhibiting proliferation and killing of cancer cells when the PTEN protein gene is delivered to brain tumor cells through recombinant NDV and expressed as a normal protein. Accordingly, the overall combination from the NP protein to the transgene cassette, the PTEN gene, and the P gene functionally provides an optimal nucleotide sequence for transduction expression and functional activity of PTEN protein gene. Various nucleotide sequences having the same functional activity will be possible, and preferably 70% or more of the same nucleotide sequence. More preferably, it will be 80% or more of the same nucleotide sequence, and most preferably, it will be a nucleotide sequence having 90% or more of functional activity.

In addition, the "recombinant Newcastle disease virus (Accession No. KCTC14496BP)" may be one into which the LVP-K1-PTEN vector represented by the nucleotide sequence represented by SEQ ID NO: 2 is introduced and includes a functionally equivalent substance. The term "functionally equivalent substance" refers to a gene or gene combination including a sequence having at least 70%, preferably at least 80%, and more preferably at least 90% of homology with a gene sequence represented by SEQ ID NO: 2 as a result of a substitution or deletion of a nucleotide and exhibiting substantially identical physiological activity to the gene having the gene sequence represented by SEQ ID NO: 2.

In addition, the present invention provides a pharmaceutical composition for prevention or treatment of brain tumors containing the recombinant Newcastle disease virus or a purified virus as an active ingredient.

Since the pharmaceutical composition of the present invention includes the above-described recombinant Newcastle disease virus, the description of the contents overlapping with the above-described recombinant Newcastle disease virus of the present invention is omitted in order to avoid the excessive complexity of the present specification due to the overlapping description.

In addition, the pharmaceutical composition may further include an immune enhancing material or adjuvant. The immune enhancing material or adjuvant may be a material that can help the treatment effect by inducing an immune response of cancer cells but is not limited thereto.

The "recombinant Newcastle disease virus (Accession No. KCTC14496BP)" may be in any form known in the pertinent field, for example, a solid form suitable for solution and injectables or suspension but is not limited thereto. Such formulations may also be formulated into an emulsified or encapsulated form for easy absorption into the body, or in the form of an aerosol or spray. They may also be incorporated into transdermal patches. Liquids or injectables may contain propylene glycol if necessary and sodium chloride in an amount sufficient to prevent hemolysis (for example: about 1%).

In addition to the therapeutic virus of the present invention, a pharmaceutically acceptable carrier or diluent may be included. Herein, the term "pharmaceutically acceptable" refers to a non-toxic composition that is physiologically acceptable and does not inhibit an action of the active ingredient when administered to humans and does not normally cause allergic reactions such as gastrointestinal disorders, dizziness, or similar reactions.

The technical fields requiring viral stability and safety as therapeutic agents are known to those skilled in the art and include, but are not limited to, proteins, sugars, and the like. Such carriers may be aqueous or non-aqueous solutions, suspensions, or emulsions. As the adjuvant, a typical or atypical organic or inorganic polymer or the like may be used. As the composition that may be added, stabilizers, antibiotics, preservatives, and the like may be used. Depending on the route of administration, the virus may be used by mixing with distilled water or a buffer solution.

The therapeutic virus may be administered via direct injection into cancer tissue or an administration route such as oral, intramuscular, subcutaneous, intravenous, etc., but is not limited thereto, and may preferably be administered through an intravenous route.

The term "subject" of the present invention refers to a subject in need of a method of control or treatment for the treatment of disease and alleviation of symptoms, and more specifically, a human, or a mammal such as a non-human primate, a mouse, a rat, a dog, a cat, a horse, or a cow.

The term "treatment" of the present invention refers to all actions such as inhibition of proliferation or death of brain tumor cells by administration of a composition according to the present invention, and delay of increase or decrease in brain tumor tissue.

The term "treatment" of the present invention refers to all actions that alleviate or beneficially change symptoms for brain tumors by administration of a composition according to the present invention.

Moreover, the present invention provides a method for producing a recombinant Newcastle disease virus, in which the method includes: inoculating the recombinant Newcastle disease virus into a host cell line; culturing the host cell line; and obtaining the recombinant Newcastle disease virus from a culture of the host cell line.

In the present invention, the recombinant viruses LVP-K1-PTEN and LVP-K2-PTEN may be recovered through a conventional virus production method. After the production of infectious clone cDNA represented by SEQ ID NO: 2 for PTEN protein expression was completed, three types of helper plasmids (NP, P, L) and modified vaccinia virus (MVA/T7) were injected into the HEp-2 cell line and cultured, followed by the recovery of the recombinant virus according to a conventional method. Transfection was performed using lipofectamine 3,000 as an injection method into the cell line, and HEp-2 cells were used as the cell line. After culturing for 3 to 4 days, the recombinant virus was recovered and inoculated into the allantoic cavity of an 8 to 10 day old SPF embryonated egg. After culturing the virus, the allantoic fluid was recovered and the virus titer was increased by culturing at least two blind passages on embryonated eggs in the same way. After purification from allantoic fluid by a conventional purification method, it was cultured in Vero76 cells selected as an appropriate cell line and used in the experiment. As for a method for identifying the expression of the PTEN protein of the recombinant virus strains LVP-K1-PTEN and LVP-K2-PTEN virus, a reverse transcription PCR method was used to identify the gene stability of the PTEN protein (FIG. 2), and mRNA expression, and Western blotting was used to identify the expression of the PTEN protein. Virus purification was performed prior to Western blotting.

Purification of the virus proceeds clarification by centrifugation after harvesting the recombinant virus culture medium. Clarification may be performed by centrifugation or microfiltration. The centrifugation may be performed under the conditions of 10,000 g, 10 minutes, and 4° C. so that supernatants may be used for the next purification process. In the case of microfiltration, a filter with a pore size of 1.0 μm to 0.2 μm may be used, and a filter with a pore size of 0.45 μm may be preferably used. As the filtration method, either dead end filtration or cross flow filtration may be used, and both methods are applicable. Recombinant virus purification is possible through known methods, including extraction through chromatography or ultrafiltration method. In the purification method using chromatography, virus purification is possible through a combination of an appropriate resin and buffer through a difference in binding power such as affinity, ion exchange, size exclusion, and hydrophobicity. Usually, virus purification is recovered by precipitating or separating the virus by ultra-high-speed centrifugation using sucrose gradient media, and the recovered virus is resuspended in THE buffer for use in the next process. Recombinant virus was purified using cation exchange resin chromatography, and after sample loading, the fraction extracted at a specific concentration was recovered through a sodium chloride concentration gradient. The recovered fraction was recovered by precipitating or separating the virus by ultra-high-speed centrifugation using sucrose gradient media, and the recovered virus was resuspended in physiological saline for injection and used in the next process.

In addition, the present invention provides a brain tumor treatment induction method including administering to a human a therapeutically effective amount of the viral composition in order to induce a treatment effect on a human brain tumor.

In addition, the treatment effect is demonstrated by a reduction or absence of clinical symptoms normally exhibited by a brain tumor, a faster recovery time or a lower duration, a difference in a low number of brain tumor cells in a sample of blood, body fluid or organ of brain tumor cells, a reduction of brain tumor tissue, and death of brain tumor cells.

In addition, the effective amount of a therapeutic agent refers to an amount capable of inducing a treatment effect and inducing effects such as a reduction of clinical symptoms caused by brain tumors in humans, reduction of cancer cells, reduction of cancer tissue, etc., and may be appropriately selected by those skilled in the art. For example, in the case of an effect amount of a therapeutic agent containing a recombinant viral composition, an amount of the purified virus may be $10^{5.0}$ TCID$_{50}$/ml to $10^{11.0}$ TCID$_{50}$/ml. More preferably, it may be $10^{8.0}$ TCID$_{50}$/ml to $10^{9.0}$ TCID$_{50}$/ml or more.

The method for inducing a treatment effect is not limited thereto, but may be inoculating the composition through oral, transdermal, intramuscular, intraperitoneal, intravenous, or subcutaneous routes. Preferably, the first and second or more compositions may be directly injected into a vein or cancer tissue. More preferably, it may be an intravenous injection. There is no limit to the number of inoculations depending on a treatment effect.

In addition, the present invention provides a method for providing information on brain tumor prevention or treatment, in which the method includes administering a recombinant Newcastle disease virus to a subject.

In addition, the present invention provides a method for evaluating a treatment effect in an animal, in which the method includes administering a recombinant Newcastle disease virus to an animal.

In addition, the method may be to measure the cancer cell killing effect using a human cancer cell line.

The cancer cell line may be a brain tumor-derived cell line, preferably a T98G cell line. In addition, patient-derived cancer cell lines may be used, and the present invention is not limited only to brain tumor-derived cell lines.

The present invention provides a method of injecting the LVP-K1-PTEN virus into a cancer tissue of a mouse transplanted with brain tumor cells, that is, a xenograft model. After generation of cancer tissue, intravenous injection or direct injection into cancer tissue may be used, and a method for measuring the effect of virus injection, such as complete remission, partial remission, or reduction of cancer tissue, may be provided.

The "LVP-K1-PTEN virus" of the present invention was deposited with the Korean Collection for Type Cultures (KCTC) on Mar. 12, 2021, and was given an Accession No.: KCTC 14496BP.

MODES OF THE INVENTION

Hereinafter, the examples of the present invention will be described in more detail with reference to the accompanying drawings. However, the following examples are only intended to embody the contents of the present invention, and the present invention will not be limited thereto.

<Example 1> Production of Recombinant NDV (LVP-K1) Genome Vector Using NDV VG/GA Strain as Basic Backbone NDV VG/GA has about 15 kb of negative-sense single-stranded RNA as genetic information and is composed of 6 ORFs, and the proteins that form a structure of the virus encode NP (nucleoprotein, SEQ ID NO: 7), P (phosphoprotein, SEQ ID NO: 8), M (matrix protein, SEQ ID NO: 9), F (fusion protein, SEQ ID NO: 10), HN (hemagglutinin-neuraminidase, SEQ ID NO: 11) and L (RNA-directed RNA polymerase, SEQ ID NO: 12) genes. After RNA isolation using a viral RNA extraction kit (Qiagen), four pairs of primers specific for genes were prepared and reverse transcription polymerase chain reaction (RT-PCR) was performed. Five pairs of primers specific to the gene are shown in Table 1 (showing the primers used during the insertion process using a restriction enzyme into a pBR322 vector after cDNA synthesis of the present invention). RT-PCR was performed at 42° C. for 1 hour and at 94° C. for 5 minutes, followed by a total of 30 cycles of 94° C. for 1 minute, 60° C. for 1 minute, and 72° C. for 1 minute, followed by reaction at 72° C. for 7 minutes. A cloning strategy for serially linking a set of cDNA fragments of four fragments is shown in FIGS. 1A and 1B.

TABLE 1

| Gene | Direction | Sequence (5`→3`) | Restriction site | SEQ ID NO. |
|---|---|---|---|---|
| Fragment 1 (L2) | Forward | ACGCGTggtctcaggttttatatgcagggaa | MlnI | 13 |
| | Reverse | TTAATTAAaccaaacaaagatttggtgaatg | PacI | 14 |
| Fragment 2 (L1) | Forward | ACTAGTtgagattctcaaggatgatggggt | SpeI | 15 |
| | Reverse | ACGCGTcgagtgcaagagactaatagtttt | MlnI | 16 |
| Fragment 3 (F-HN) | Forward | GGC GCC attatcggtggtgtagctctcgg | Kas I | 17 |
| | Reverse | ACTAGTaaagggacgattctgaattccccg | SpeI | 18 |
| Fragment 4 (P-M-F) | Forward | CCGCGGaaacagccaagagagaccgcagaa | SacII | 19 |
| | Reverse | GGCGCCaaccgggatccagaatcttctacccgt | Kas I | 20 |
| Fragment 5 (NP-P) | Forward | GTTTAAACaccaaacagagaatccgtaagg | PmeI | 21 |
| | Reverse | CCGCGGctttgttgactccctgttgttga | SacII | 22 |

In order to increase the reconstitution efficiency of the vector, cloning was performed by locating PacI and PmeI restriction enzymes having different recognition sites and cleavage sites into a modified pBR322 vector, which is preferably a low-copy-number plasmid. The modified pBR322 vector was preferably under the control of a T7 RNA polymerase promoter and was located so that it was terminated by the hepatitis delta virus (HDV) antigenome ribozyme and T7 terminator gene used to split RNA at the terminus of the NDV genome to enable viral encapsidation and packaging. In addition, the complete genome sequence of the NDV VG/GA strain was included to ensure accurate transcription.

Thereafter, as shown in Table 2 (indicating the primers used for constructing the LVP-K1 vector of the present invention) and Table 3 (indicating the primers used for constructing the LVP-K2 vector of the present invention) below, the genes were divided into four fragments and a transgene cassette was introduced between the NP gene and the P gene and a transgene cassette was introduced between the P gene and the M gene using a cloning strategy to successively link the cDNA fragment sets.

TABLE 2

| Gene | Direction | Sequence (5`→3`) | SEQ ID NO. | Size (bp) |
|---|---|---|---|---|
| Fragment 1 (pBR322-NP) | Forward | TTCTCGCTTCCGGCGGCATC | 23 | 5,036 |
| | Reverse | CCGCTTCTACCCGTATTTTTTCTAAGCAGAGGAATTGGGATGACCTC | 24 | |
| Fragment 2 (P-M) | Forward | TACGGGTAGAAGCGGCCGCGGCCGGCCCCACACCCCACCCCTCAATCC | 25 | 2,938 |
| | Reverse | CCGGGATCCAGAATCTTCTACCC | 26 | |
| Fragment 3 (F-HN) | Forward | GATTCTGGATCCCGGTTGGCG | 27 | 5,578 |
| | Reverse | CCGCCATCACTTGACAGTTCC | 28 | |
| Fragment 4 (L) | Forward | GTCAAGTGATGGCGGAAGGG | 29 | 5,256 |
| | Reverse | CGCCGGAAGCGAGAAGAATC | 30 | |

TABLE 3

| Gene | Direction | Sequence (5`→3`) | SEQ ID NO. | Size (bp) |
|---|---|---|---|---|
| Fragment 1 (pBR322-NP-P) | Forward | TTCTCGCTTCCGGCGGCATC | 31 | 6,545 |
| | Reverse | TTCTACCCGTATTTTTTCTTAAGTTTGCAGAGAGG | 32 | |
| Fragment 2 (M-F) | Forward | AAAATACGGGTAGAAGCGGCCGCCCAAGGTCCAACACCCCGAG | 33 | 3,728 |
| | Reverse | GACGTCGCTAGCATCATCTAC | 34 | |
| Fragment 3 (HN-L) | Forward | GATGCTAGCGACGTCACATC | 35 | 3,245 |
| | Reverse | CCGCCATCACTTGACAGTTCC | 36 | |
| Fragment 4 (L) | Forward | GTCAAGTGATGGCGGAAGGG | 37 | 5,626 |
| | Reverse | CGCCGGAAGCGAGAAGAATC | 38 | |

RNA-dependent RNA polymerase initiates transcription in a sequential manner by the stop-start mechanism IGS (GE-IG-GS) between genes. In GS, the transcriptional reinitiation is not complete, so the level of transcription of mRNA located at the 3' terminus is high. Accordingly, the higher the 3' terminus, the higher the mRNA transcription level, and the level decreases as it goes towards the 5' terminus. Accordingly, a new foreign gene insertion between the NP gene and the P gene results in a higher level of mRNA transcription and foreign protein translation than between the P gene and the M gene and between the HN gene and the L gene, and thus the gene insertion between NP-P is more preferable.

The four cDNA fragments had the same nucleotide sequence at the end of 15 bp, and the transgene cassette consisted of an IGS (GE-IG-GS) sequence (SEQ ID NO: 5) and a multiple cloning site (MCS). LVP-K1 (SEQ ID NO: 1) and LVP-K2 vectors for foreign gene insertion were constructed by inserting them between the NP gene and the P gene (LVP-K1) and between the P gene and the M gene (LVP-K2) using an overlap cloning method.

<Example 2> Construction of Recombinant NDV cDNA Containing PTEN Gene

A recombinant Newcastle disease virus containing the PTEN protein gene in Newcastle disease virus (NDV) virus cDNA was constructed.

The LVP-K1 (NP-MCS-P) vector and the LVP-K2 (P-MCS-M) vector were inserted between the NP and P genes (LVP-K1-PTEN vector) and between the P gene and M gene (LVP-K2-PTEN vector) of the NDV cDNA backbone prepared after obtaining the required PTEN-containing DNA fragment with Fse I restriction enzyme for LVP-K1 (NP-MCS-P) vector and Not I restriction enzyme for the LVP-K2 (P-MCS-M) vector. Afterward, it was identified that the completed plasmid was 100% identical through whole gene sequencing.

<Example 3> Production of Recombinant Newcastle Disease Virus

Individual clones (NP, P, L) of the NDV transcriptase complex were cloned into pBR322 vector and used as helper plasmids (pBR322-NP, pBR322-P, pBR322-L). On the previous day, HEp-2 cells were prepared at 5×10⁵ cells/well in a 6-well plate, and the modified vaccinia virus (MVA-T7) was infected at 1 MOI (multiplicity of Infection). In the cell line, each of 2.5 μg, 1.5 μg, 0.5 μg, and 5 μg of pBR322-NP, pBR322-P, pBR322-L Helper plasmids expressing proteins by the T7 promoter and LVP-K1-PTEN or LVP-K2-PTEN vectors, which are plasmids containing the PTEN protein gene were transformed by mixing them with lipofectamine 3000 (Invitrogen) at an appropriate ratio. Thereafter, the HEp-2 cell supernatant was harvested after culture at 37° C. and 5% $CO_2$ conditions for 3 to 4 days. Then, 9-11 days old SPF embryonated eggs were inoculated into the allantoic cavity, and allantoic fluid was collected 4 days after inoculation.

Figure 2:
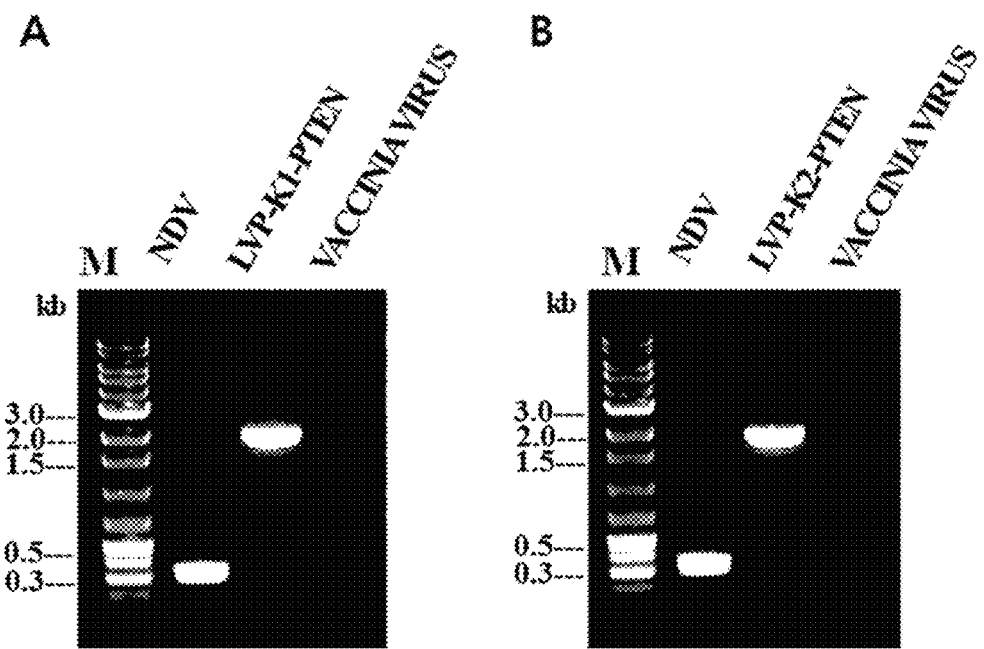
Figure 3:
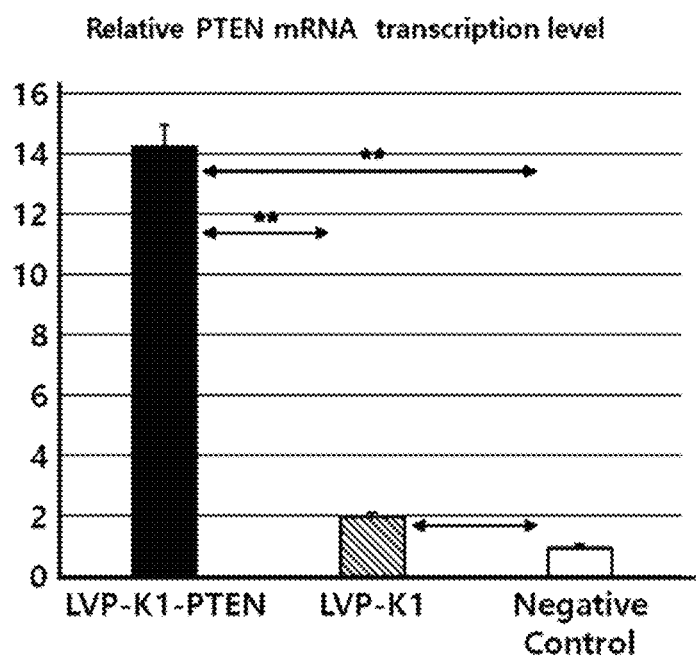

Thereafter, in order to remove the vaccinia virus, the allantoic fluid diluted at $10^{-3}$ with PBS was inoculated into the allantoic cavity of 9-11 days old SPF embryonated eggs, respectively, and the allantoic fluid was collected 4 days after inoculation to conduct a virus identification experiment. For the virus identification experiment, after isolation of the allantoic fluid using a Viral RNA extraction kit (Qiagen), 5 μl of the extracted RNA and 1 μl of each of the forward and reverse primers in Table 4 below (primers necessary for identifying the construction of the recombinant NDV(LVP-K1-PTEN and LVP-K2-PTEN) of the present invention) were used for reaction at 42° C. for 1 hour and at 94° C. for 5 hours with ONE-STEP RT-PCR. Thereafter, a total of 35 cycles of reaction were carried out at 94° C. for 1 minute, at 60° C. for 1 minute, and at 72° C. for 1 minute, and then at 72° C. for 7 minutes for identification. The results are shown in FIG. 2.

As shown in FIGS. 2A and 2B, it was identified that the vaccinia virus was removed, and only Newcastle disease virus and recombinant Newcastle disease virus LVP-K1-PTEN (SEQ ID NO: 2) and LVP-K2-PTEN virus remained.

Table 5 (primers for inserting the PTEN gene into the LVP-K1 vector) and Table 6 (primers for inserting the PTEN gene into the LVP-K2 vector) show primers for inserting the PTEN gene into the vector.

TABLE 4

| Gene | Direction | Sequence (5`→3`) | SEQ ID NO. | Size (bp) |
|---|---|---|---|---|
| NDV check | Forward | CCACAATTCCAAGATAACCGGAG | 39 | 327 |
| | Reverse | GCTGCCACAATCAGATGCCTTTG | 40 | |
| NP-PTEN-P check | Forward | AACAGATCACAAGGGCAACCG | 41 | 1,822 |
| | Reverse | TGGTTTTCCCTGGGCCGTAATT | 42 | |
| P-PTEN-M check | Forward | GGCAAGCGGGCCTGATATAGG | 43 | 1,734 |
| | Reverse | CTTCCCGTCCCCTGTGTCTTG | 44 | |
| Vaccinia virus check | Forward | ATGACGATGAAAATGATGGTACATA | 45 | 1,059 |
| | Reverse | CTCCAATACTACTGTAGTTGTAAGG | 46 | |

TABLE 5

| Gene | Direction | Sequence (5`→3`) | SEQ ID NO. | Size (bp) |
|---|---|---|---|---|
| Kozak PTEN (1st PCR) | Forward | GCCACCATGACAGCCATCATCAAAG | 47 | 1,221 |
| | Reverse | AGAAGCGGCCGCGGCCGGCCACCATGACAGCC | 48 | |
| Fse 1 Kozak PTEN (2nd PCR) | Forward | GCCTCAGACTTTTGTAATTTGTGTATG | 49 | 1,258 |
| | Reverse | GTTGGACCTTGGTATGGCCGGCCTCAGACTTTTGTAATTTGTG | 50 | |

TABLE 6

| Gene | Direction | Sequence (5'→3') | SEQ ID NO. | Size (bp) |
|---|---|---|---|---|
| Kozak PTEN (1st PCR) | Forward | GCCACCATGACAGCCATCATCAAAG | 47 | 1,221 |
| | Reverse | CGCTCAGACTTTTGTAATTTGTGTA | 48 | |
| Not I Kozak PTEN (2nd PCR) | Forward | ATACGGGTAGAAGCGGCCGCCACCATGACAGCC | 49 | 1,254 |
| | Reverse | TGGACCTTGGGCGGCCGCTCAGACTTTTGTAATTTG | 50 | |

<Example 4> Recombinant Newcastle Disease Virus LVP-K1-PTEN Culture and Purification Vero76 cells were cultured at 3×10$^5$ cells/ml, and then inoculated with the recombinant virus 0.05 MOI (multiplicity of Infection) on the next day to obtain the highest titer of the virus supernatant after 2 days. Thereafter, the virus supernatant was centrifuged at 5,000 g at 4° C. for 10 minutes to remove floating materials, and the supernatant was collected. The collected supernatant was ultracentrifuged at 32,000 rpm at 4° C. for 3 hours to concentrate the recombinant virus, and after removing the supernatant, the collected supernatant was resuspended in THE buffer (10 mM Tris-HCl, 20 mM NaCl, 1 mM EDTA). The concentrated virus was subjected to ultracentrifugation at 32,000 rpm and 4° C. for 2 hours using a 30 to 60% sucrose gradient method. Recombinant virus was obtained at 40-50%. Finally, the obtained recombinant virus was subjected to ultracentrifugation once more at 32,000 rpm at 4° C. for 2 hours to remove sucrose to purify recombinant Newcastle disease virus LVP-K1-PTEN (SEQ ID NO: 2) and LVP-K2-PTEN.

<Example 5> T98G Cell Culture and Vero Cell Culture

In order to identify the cancer cell killing effect, T98G (CRL-1690™, ATCC) brain tumor cells were used. T98G cells were cultured as follows. T98G cells were cultured using the minimum essential medium (MEM, Gibco, USA) containing penicillin-streptomycin (Gibco, USA) and 10% FBS for cell culture, in a 37° C. incubator (5%, CO$_2$) using a 175 T flask. When the cells grow to form a 70-80% monolayer in the flask, the cells were maintained through subculture from 1:4 to 1:6. Seeding density was about 2 to 4×10$^4$ cells/ml. Vero cells (Vero 76 KCLB No. 21587) were cultured using a Minimum essential medium (MEM, Gibco, USA) containing penicillin-streptomycin (Gibco, USA) and 10% FBS for cell culture, and a 175 T flask. When the cells grow to form a monolayer of 70 to 80% or more, subculture was proceeded and maintained. The split ratio of Vero76 cells may be up to 1:8 and the seeding density is 1×10$^4$ cells/ml.

<Example 6> Identification of Proliferation of Recombinant Virus Using Vero Cells Comparative experiments on the proliferation of LVP-K1 (SEQ ID NO: 1) virus and LVP-K1-PTEN (SEQ ID NO: 2) virus were performed using Vero cells prepared in Example 5. In general, viruses into which a foreign gene is inserted often do not proliferate well. The proliferation of the virus into which the PTEN gene was inserted was compared and identified. After removing the culture medium of Vero 76 cell (175 T flask) that has formed a monolayer of 70 to 80% or more, 10 ml of serum-free MEM medium was added to the flask and gently shake to wash the cells. After repeating this process 2 to 3 times, 5 ml (1 MOI) of LVP-K1 (SEQ ID NO: 1) virus and LVP-K1-PTEN (SEQ ID NO: 2) virus was added to the flask in advance and shook at intervals of 10 minutes in a 37° C. incubator to sensitize the virus for 1 hour. After removing the virus solution, 10 ml of serum-free MEM was put into the flask to remove the remaining virus solution, and then again, 50 ml of MEM supplemented with 5% FBS was added, and 1 ml of culture medium was collected from each flask every 4 hours, and the virus titer was measured by the TCID$_{50}$ measurement method.

<Example 7> Identification of PTEN Gene of Virus Cultured in Vero Cells

In order to identify that recombinant Newcastle disease viruses LVP-K1-PTEN and LVP-K2-PTEN cultured in Vero cells are maintained without PTEN gene loss during culture in Vero cells, the viruses, which have been subcultured for seven generations, were used to identify genes by RT-PCR method using the primers in Table 4 above for PTEN gene amplification. The gene obtained through electrophoresis was identified to be a PTEN gene through the sequencing method.

<Example 8> Evaluation of mRNA Expression Level of LVP-K1-PTEN Gene Using Real Time qPCR Method Pre-prepared T98G cells were inoculated with LVP-K1 (SEQ ID NO: 1) virus and LVP-K1-PTEN (SEQ ID NO: 2) virus at 1 MOI, and one flask was cultured for 6 hours without inoculating any virus. After the culture was completed, RNA was obtained from all flasks using the AccuPrep®Universal RNA extraction kit (Bioneer), and then primers and probes of Table 7 below (primers and probes for indicating the relative transcriptional amounts of PTEN mRNA in LVP-K1-PTEN and LVP-K1 virus-infected T98G cells of the present invention) were added and real-time PCR was performed. The expression level of mRNA was identified by measuring the CT value for each sample. The real time qPCR conditions were as follows. After reacting at 42° C. for 10 minutes and at 95° C. for 2 minutes, a total of 40 cycles of reaction of fluorescence level measurement were performed for 10 seconds at 95° C. and 1 minute at 59.8° C. A CFX Connect™ Real-Time System (cat. No. 1855201 Bio-Rad, USA) was used.

TABLE 7

| Gene | Direction | Sequence (5'→3') | SEQ ID NO. | Size (bp) |
|---|---|---|---|---|
| PTEN Real-time | Forward | TCCCAGTCAGAGGCGCTATGT | 51 | 152 |
| | Reverse | GGCAGACCACAAACTGAGGA | 52 | |
| | Probe | TGCAAGTTCCGCCACTGAACA | 53 | — |

From the results shown in Table 3, it was understood that mRNA expression in the LVP-K1-PTEN virus-inoculated sample having the PTEN gene was higher than in the LVP-K1 virus-inoculated and non-virus-inoculated T98G cell line (control group).

<Example 9> Comparison of Expression Level of PTEN Protein Through Western Blotting of PTEN Protein Three types of viruses were inoculated into pre-prepared T98G cells, and the expression of PTEN protein in non-inoculated T98G cells was compared. There are three types of viruses: LVP-K1-PTEN (PTEN gene inserted between NP and P genes, SEQ ID NO: 2), LVP-K2-PTEN (PTEN gene inserted between P and M genes), and LVP-K1 (SEQ ID NO: 1) virus without PTEN gene inserted. Western blotting was conducted because it was determined that the amount of protein expression could be compared through an experiment in which the quantitative protein amount could not be accurately evaluated or a relative evaluation. Three types of viruses whose titer was measured in the same manner as in Example 6 or Example 8 were prepared in the T98G cell line that formed a monolayer of 80% or more, and inoculated at an MOI of 1, and then 9 hours later, the entire culture medium was frozen and thawed 3 times or more. After repeating the same, a sample was collected, the protein was separated through a conventional SDS-PAGE (Gel concentration of 12%), and the protein was transferred to a PVDF membrane (25 A, 15 minutes) using a transblottor (Thermo fisher). PVDF membrane was blocked with 1% BSA solution and then performed according to a conventional western blotting method. A PTEN monoclonal antibody was used as the primary antibody specifically binding to PTEN (Cat No. ab32119, Abcam). Anti-rabbit IgG goat horse peroxidase conjugate antibody (Invitrogen) was used as the secondary antibody to identify the protein-specific developmental reaction, and the antibody concentration was used as recommended by the manufacturer. After the secondary antibody reaction, an appropriate amount of ECL (enhanced chemiluminescence, Bio-Rad) solution was added as a color developer, and when the color developed, the protein was identified using ChemiDoc™ MP Imaging System (Bio-Rad).

Figure 4:
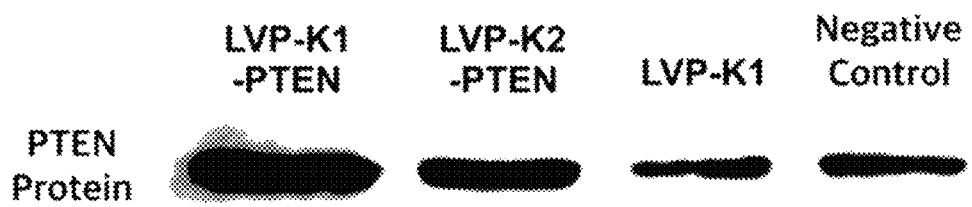

As shown in the results of FIG. 4, it can be seen that the expression level of PTEN protein after virus infection was color-developed most clearly in the LVP-K1-PTEN virus, in which the PTEN gene was inserted between the NP and P genes, so that a greater amount of protein was expressed in T98G cells than in other test groups.

<Example 10> Identification of Brain Tumor Cell Killing Effect Due to Infection with LVP-K1-PTEN Virus into which PTEN Gene is Introduced In order to identify the apoptosis effect of brain tumor cells T98G cells caused by LVP-K1-PTEN virus infection, an MTT assay experiment was performed. The MTT assay method was performed according to the conventional MTT assay method, and detailed experimental procedures are described. In a 96-well plate, $1 \times 10^4$ T98G cells per well were cultured for 24 hours using minimum essential medium (MEM, Gibco, USA) containing penicillin-streptomycin (Gibco, USA) and 10% FBS for cell culture in a 37° C. incubator (5% $CO_2$), and LVP-K1-PTEN virus and LVP-K1 virus were infected to be made at 0.1, 1, 2.5 and 5 MOIs. For the reliability of the results, 4 wells of the same condition were prepared to proceed. After infection, the cells were cultured in a 37° C. incubator (5% $CO_2$), and 96 hours after infection, 20 μl of MTT solution (CellTiter 96® AQueous One solution Cell Proliferation Assay, Bio-Rad, USA) was added to each well and the cells were cultured for 1 hour in an incubator (5% $CO_2$). Cell death was measured by measuring the absorbance of light having a wavelength of 490 nm using an iMark Microplate Reader (Bio-Rad, USA).

Figure 5:
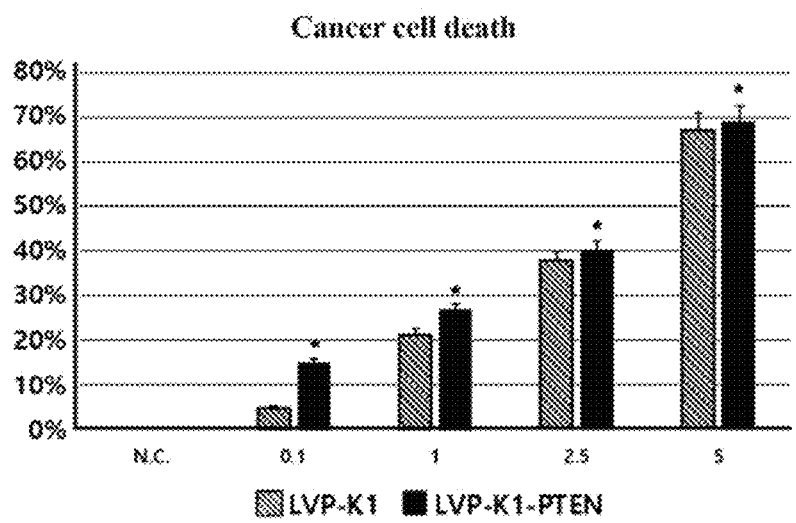

As a result, as shown in FIG. 5, as a result of the MTT assay, the virus into which the PTEN gene was inserted had a higher cancer cell killing effect than the virus without the PTEN virus inserted. In particular, the difference in the cancer cell killing effect shows a difference as the concentration of the virus inoculated into the cells is low. This is because the recombinant NDV, LVP-K1 virus, also has an original oncolytic effect, so there is no difference at high concentrations. The high killing effect of the virus with the PTEN gene inserted at MOI 1 or less is produced because normal PTEN protein is expressed in cancer cells by the PTEN gene transferred to the virus, and this PTEN protein is considered to have an effect on apoptosis by increasing the apoptosis effect of cancer cells.

Figure 6:
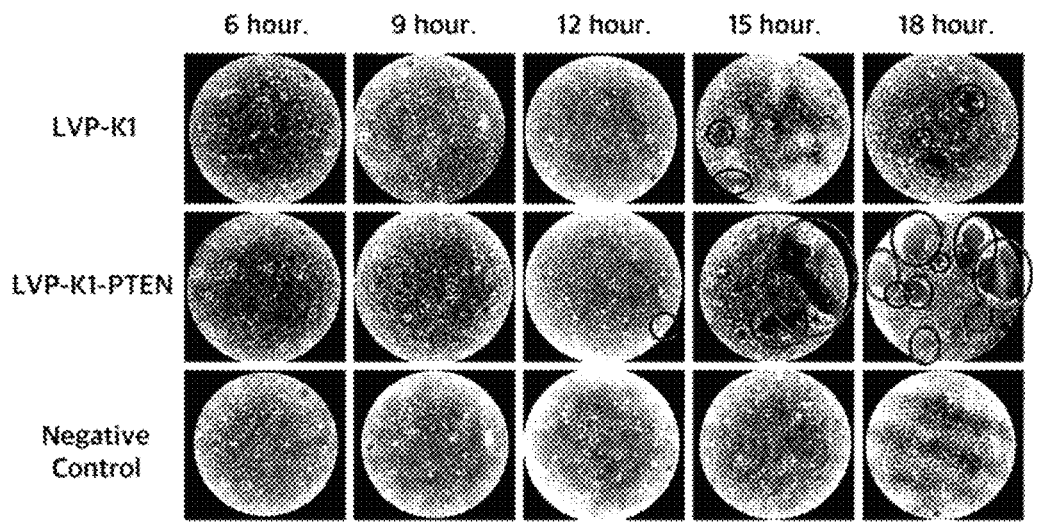
FIG. 6 is a view showing illustrating a cytopathic effect of T98G cells infected with LVP-K1-PTEN and LVP-K1 viruses of the present invention through a microscope.

After inoculation of the virus into the T98G cell culture medium, microscopic observation was performed to observe the cytopathic effect. T98G cells were cultured in a 6-well plate to form a monolayer of 90% or more, and then each virus was inoculated at 1 MOI to observe the T98G cytopathic effect under a microscope. Cytopathic effect (CPE) was observed 3 hours earlier in LVP-K1-PTEN virus-inoculated cells with PTEN gene than LVP-K1 virus-inoculated cells without PTEN gene. As a result of observation up to 18 hours thereafter, a faster cytopathic effect was observed in LVP-K1-PTEN virus-inoculated cells (see FIG. 6).

<Example 11> Identification of Cancer Cell Proliferation Inhibitory Effect of LVP-K1-PTEN Virus Using T98G Cell Transplantation Xenograft Model Mice The cancer tissue growth inhibitory effect of LVP-K1-PTEN virus was measured using a xenograft model. $6 \times 10^7$ cells of cultured T98G cells were dissolved in 100 ul MEM and were mixed with 100 ul Matrigel (Corning) and inoculated into the left shoulder region of mice. For the mice used, 20 SPF female BALB/c nude mice weighing about 14 to 19 g were purchased from SLC (Japan) and randomly divided into 4 mice per group for experiments. Each experimental group consisted of two groups in which LVP-K1-PTEN virus introduced with the PTEN gene was injected directly into the tail vein and cancer tissue, two groups in which LVP-K1 virus without PTEN gene introduced was injected directly into the tail vein and cancer tissue, and a PBS inoculation group (control group). The concentration of the inoculated virus was all 10" $TCID_{50}$/ml, and 100 ul each was inoculated. Virus inoculation was performed twice at an interval of 2 days from when the cancer tissue size reached an average of 120 to 150 mm³ on the 7th day after T98G cell inoculation, and cancer tissue changes were observed every day for 7 days. The size of the cancer tissue was calculated using the formula $47E/3 \times (\text{smallest diameter}/2)^2 \times (\text{largest diameter}/2)^2$.

Figure 7:
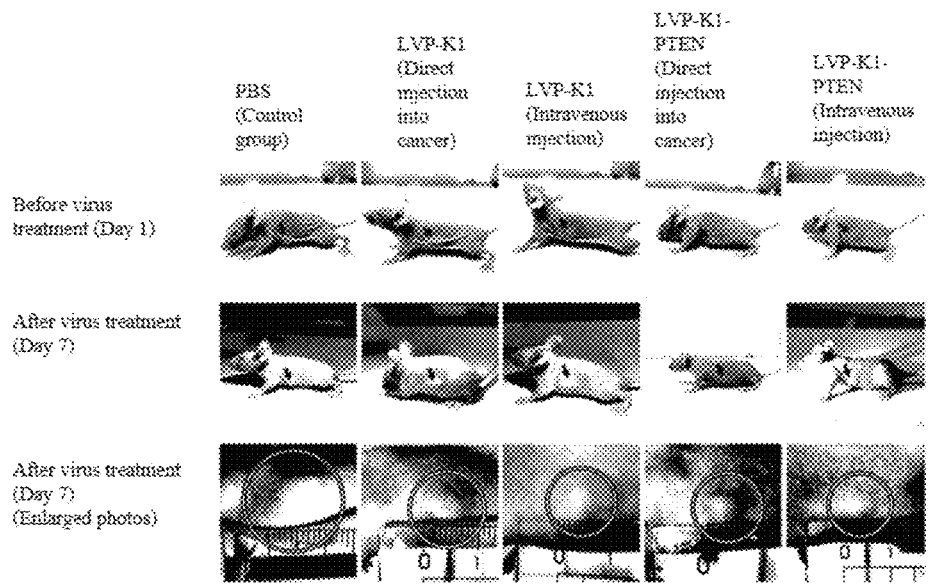
FIG. 7 is a view showing a reduction in cancer size by directly injecting LVP-K1-PTEN and LVP-K1 viruses of the present invention into the tail vein or cancer in xenograft.
Figure 8A:
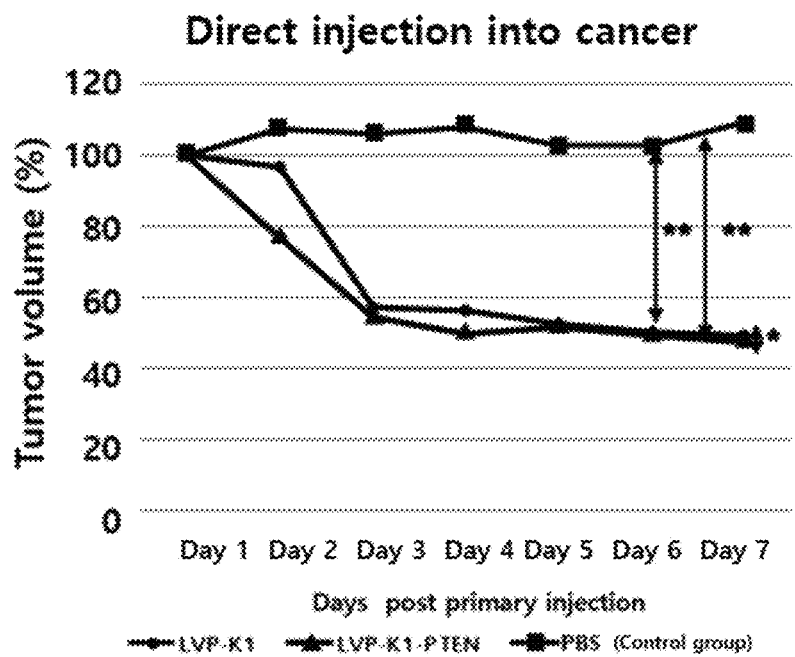
FIGS. 8A and 8B show graphs for each day of reduction in cancer size by injection of the LVP-K1-PTEN and LVP-K1 viruses of the present invention directly into the cancer in xenograft (FIG. 8A) or by injection into the tail vein (FIG. 8B) (* indicates P value 0.05 or less, and ** indicates P value 0.01 or less).
Figure 8B:
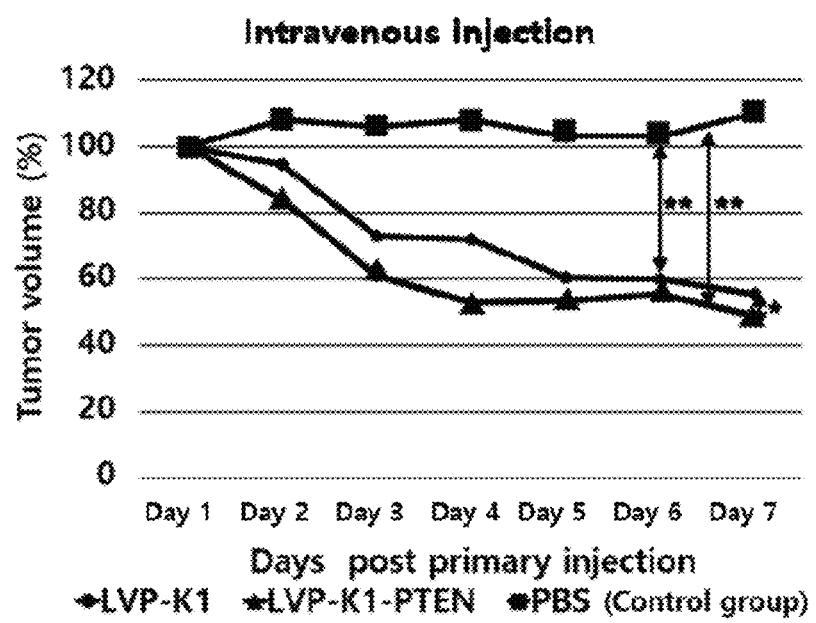

Though table 8 (LVP-K1-PTEN and LVP-K1 viruses of the present invention were injected directly into the tail vein or cancer in xenograft to reduce cancer size), and FIGS. 7, 8A, and 8B, the fastest and most effective reduction in cancer tissue was observed in the LVP-K1-PTEN virus-inoculated group into which the PTEN gene was introduced. One unusual feature is that it is generally known that direct injection into cancer tissue shows a better effect than intravenous injection, however, according to the results of this experiment, it was identified that intravenous injection could inhibit the proliferation of cancer cells without much difference compared to the case of direct injection into cancer tissues.

TABLE 8

| Tumor size (%) | Day 1 | Day 2 | Day 3 | Day 4 | Day 5 | Day 6 | Day 7 |
|---|---|---|---|---|---|---|---|
| PBS (Control group) | 100 | 107.621 | 105.888 | 107.954 | 102.954 | 102.856 | 109.560 |
| LVP-K1 (Direct cancer injection) | 100 | 96.875 | 57.359 | 56.325 | 52.708 | 50.171 | 49.270 |
| LVP-K1-PTEN (Direct cancer injection) | 100 | 76.697 | 54.272 | 49.784 | 51.631 | 48.998 | 47.472 |
| LVP-K1 (Intravenous injection) | 100 | 94.210 | 72.928 | 71.702 | 60.406 | 60.040 | 55.309 |
| LVP-K1-PTEN (Intravenous injection) | 100 | 83.948 | 60.926 | 52.903 | 53.490 | 55.060 | 48.916 |

In conclusion, it was identified that cancer cell proliferation inhibitory effect can be obtained through the production of a novel cancer treatment viral vector using the NDV virus and a virus using the same that does not cause an immune response and does not generate antibodies in mammals. There are many NDV viruses that disappear from normal cells without reaching cancer cells due to innate immunity immediately after infection, which is a major disadvantage and advantage of NDV virus. In addition, due to the dilution effect of intravenous injection, it is a very important task to develop a recombinant NDV virus, rather than a simple recombinant virus that has been used already, that is expressed as a protein in cancer cells to increase efficacy such as cancer cell proliferation inhibitory effect, apoptosis induction, and immune response induction by inserting various genes. Further research will be needed in the future for further development.

The present invention demonstrates that there may be an oncolytic function to some extent in cancer cells in which the normal PTEN protein function is lost due to PTEN gene mutation in brain tumors and the NDV recombinant virus capable of additionally introducing a PTEN gene and passing a brain blood barrier along the nervous system is produced and the effect thereof is improved.

The disclosed embodiments should be considered in an illustrative in all aspects rather than a restrictive perspective. The scope of the present invention is defined by the following claims rather than by the preceding description. It should be interpreted that all changes or modifications derived from the meaning and scope of the claims and their equivalents are included in the scope of the present invention.

ACCESSION NO

Depository Institution: Korean Collection for Type Cultures (KCTC) of Korea Research Institute of Biotechnology and Bioscience
Accession No.: KCTC14496BP
Deposit Date: Mar. 12, 2021

The invention claimed is:

1. An LVP-K1-PTEN vector having a nucleotide sequence of SEQ ID NO: 2.

2. A recombinant Newcastle disease virus comprising the vector of claim 1.

3. A pharmaceutical composition of treating brain tumors, the pharmaceutical composition comprising the recombinant Newcastle disease virus of claim 2 as an active ingredient.

4. The pharmaceutical composition of claim 3, wherein the composition has a cancer cell killing effect.

5. The pharmaceutical composition of claim 3, wherein the composition has an inhibitory effect on cancer cell proliferation.

6. A method for treating a brain tumor comprising administering the composition of claim 3 to a subject other than a human in need thereof.

7. A method for producing a recombinant Newcastle disease virus, the method comprising inoculating the recombinant Newcastle disease virus of claim 2 into a host cell line; culturing the host cell line; and obtaining the recombinant Newcastle disease virus from a culture of the host cell line.

* * * * *